United States Patent [19]
Brooks et al.

[11] Patent Number: 5,434,068
[45] Date of Patent: Jul. 18, 1995

[54] METHOD FOR CLONING AND PRODUCING THE BGLII RESTRICTION ENDONUCLEASE AND MODIFICATION METHYLASE

[75] Inventors: Joan E. Brooks, Beverly; Daniel F. Heiter, Groveland; Brian P. Anton, Beverly, all of Mass.

[73] Assignee: New England Biolabs, Inc., Beverly, Mass.

[21] Appl. No.: 17,664

[22] Filed: Apr. 9, 1993

[51] Int. Cl.$^6$ .............. C12N 9/22; C12N 15/55; C12N 1/21; C12N 15/63
[52] U.S. Cl. ................. 435/194; 435/252.33; 435/320.1; 435/193; 536/23.2
[58] Field of Search ............ 435/199, 193, 252.33, 435/320.1; 536/23.2

[56] References Cited
PUBLICATIONS

Roberts and Macelis, Nucl. Acids Res., 20:2167–2180 (1992).
Luria and Human, J. Bacteriol., 64:557–569 (1952).
Bertani and Weigle, J. Bacteriol., 65:113–121 (1953).
Arber and Linn, Ann. Rev. Biochem., 38:467–500 (1969).
Boyer, Ann. Rev. Microbiol., 25:153–176 (1971).
Smith, Paabs Revista, 5:313–318 (1976).
Stein et al., J. Bacteriol., 174:4899–4906 (1992).
Meselson, Ann. Rev. Biochem., 41:447–466 (1972).
Smith, Science, 205:455–462 (1979).
Roberts, CRC Crit. Rev. Biochem., 4:123–164 (1976).
Smith and Nathans, J. Mol. Biol., 81:419–423 (1973).
Bougueleret et al., Nucl. Acids Res., 12:3659–3676 (1984).
Theriault and Roy, Gene, 19:355–359 (1982).
Gingeras and Brooks, Proc. Natl. Acad. Sci. USA, 80:402–6 (1983).
Blumenthal et al., J. Bacteriol., 164:501–509 (1985).
Mann et al., Gene, 3:97–112 (1978).
Walder et al., Proc. Natl. Acad. Sci. USA, 78:1503–1507 (1981).
Howard et al., Nucl. Acids Res., 14:7939–7951 (1986).
Slatko et al., Nucl. Acids Res., 15:9781–9796 (1987).
Kiss et al., Nucl. Acids Res., 13:6403–6421 (1985).
Lunnen et al., Gene, 74:25–32 (1988).
Wilson, Nucl. Acids Res., 19:2539–2566 (1991).
Brooks et al., Nucl. Acids Res., 19:841–850 (1991).
Raleigh and Wilson, Proc. Natl. Acad. Sci., 83:9070–9074 (1986).
Noyer-Weidner et al., Mol. Gen. Genet., 205:469–475 (1986).
Waite-Rees et al., J. Bacteriol., 173:5207–5219 (1991).
Wilson and Young, in Schlessinger (ed.), Microbiology-1976, American Society for Microbiology, pp. 350–357 (1976).
Pirrotta, Nucl. Acids Res., 3:1747–1760 (1976).
Duncan et al., J. Bacteriol., 134:338–344 (1978).
Wang and Kushner, Gene, 100: 195–199 (1991).
Chang and Cohen, J. Bacteriol., 134:1141–1156 (1978).
Simons et al., Gene, 53:85–96 (1987).
Janssen and Bibb, Gene, 124:133–134 (1993).
Raleigh et al., Nucl. Acids Res., 16:1563–1575 (1988).
Sanger et al., Proc. Natl. Acad. Sci. USA, 74:5463–5467 (1977).
Sanger and Coulson, FEBS Letters, 87:107–110 (1978).
Bickle et al., Methods in Enzymology, 65(16):132–138 (1980).
Suggs, S. V. et al (1981) Proc. Natl. Acad. Sci., USA 78(11), 6613–6617.

*Primary Examiner*—Charles L. Patterson, Jr.
*Attorney, Agent, or Firm*—Gregory D. Williams; David G. Conlin

[57] ABSTRACT

The present invention is directed to a method for cloning and producing the BglII endonuclease by: 1) introducing the restriction endonuclease gene from *Bacillus globigii* into a host whereby the restriction gene is expressed; 2) fermenting the host which contains the plasmid encoding and expressing the BglII restriction endonuclease activity; and 3) purifying the BglII restriction endonuclease from the fermented host which contains the plasmid encoding and expressing the BglII restriction endonuclease.

7 Claims, 8 Drawing Sheets

METHOD FOR CLONING AND PRODUCING THE BGLII RESTRICTION ENDONUCLEASE AND MODIFICATION METHYLASE

BACKGROUND OF THE INVENTION

The present invention relates to recombinant DNA which encodes the BglII restriction endonuclease and modification methylase, and the production of these enzymes from cells containing the recombinant DNA.

Restriction endonucleases are now one of the foremost tools of molecular biology. They occur naturally in a wide variety of bacteria, both eubacteria and archaebacteria (Roberts and Macelis, Nucl. Acids Res. 20: 2167–2180, (1992)), and when purified, can be used to cut DNA in a sequence-specific manner into precise fragments. By use of the large number of restriction enzymes now available commercially, DNA molecules can be uniquely identified and fractionated into component genes.

Restriction endonucleases are a component of restriction-modification (RM) systems, which have been extensively studied for over forty years (Luria and Human, J. Bacteriol. 64: 557–569, (1952); Bertani and Weigle, J. Bacteriol. 65: 113–121, (1953)). The systems usually contain a second component, the modification methylase (Arber and Linn, Ann. Rev. Biochem., 38: 467–500, (1969); Boyer, Ann. Rev. Microbiol. 25: 153–176, (1971)). It is thought that in nature RM systems act as "bacterial immune systems" that destroy foreign DNA entering cells (Smith, PAABS REVISTA 5: 313–318, (1976)). However, individual bacteria have been known to contain as many as seven different RM systems and this apparent redundancy suggests that these systems serve other functions as well (Stein et al., J. Bacteriol. 174: 4899–4906, (1992)).

In the bacterium, the restriction endonuclease scans incoming DNA for a specific recognition sequence and produces double stranded scissions in the DNA molecule (Meselson, Ann. Rev. Biochem. 41: 447–466, (1972)). The modification methylase acts to protect the bacterium's own DNA against the action of its restriction counterpart. The methylase recognizes and binds the same DNA sequence as its corresponding endonuclease; however, instead of cleaving, it methylates a specific residue within the recognition sequence, thereby preventing endonucleolytic binding or cleavage (Smith, Science 205: 455–462, (1979)). In this manner, the bacterial host DNA is rendered completely resistant to cleavage by the restriction endonucleases within the cell.

Initially the term "RM system" was applied only to systems in which the components had been genetically defined. However, the term has now come to refer to any site-specific endonuclease isolated from a bacterium. In many cases the existence of a modification methylase component is assumed without any rigorous proof (Roberts, CRC Crit. Rev. Biochem. 4: 123–164, (1976)).

When it became obvious that a large number of restriction enzymes would be isolated from a variety of bacteria, Smith and Nathans (J. Mol. Biol. 81: 419–423, (1973)) devised a nomenclature that, with minor modifications, is still being used today. A restriction enzyme is named with a three letter designation that abbreviates the genus and species from which it was isolated. When necessary, a fourth letter is added to designate the strain (like Hind). Roman numerals following the system name are assigned to differentiate multiple enzymes from the same source. The prefixes R and M refer to restriction endonuclease or modification methylase, respectively, but are usually not included. When the three letter designation is used without prefix, it is understood to refer to the endonuclease.

Restriction endonucleases, and to a lesser extent, DNA methylases, have become invaluable reagents for genetic engineering. As the field of biotechnology has grown and developed, there has been a growing commercial incentive to mass produce these enzymes. However, mass production of restriction enzymes from their native organisms is often difficult for several reasons. First, many organisms produce several RM systems, and biochemically separating the different products is often problematic. Second, in addition to multiple restriction systems, bacteria can also produce other nucleases and DNA binding proteins which are difficult to remove biochemically from restriction enzyme preparations. Third, the amount of a particular enzyme produced by an organism can be highly variable, and may vary with growth conditions. Finally, some bacteria may be difficult, expensive, or even dangerous to grow. To solve these problems and reproducibly obtain restriction enzymes in abundance, the techniques of genetic engineering have been applied to create highly productive strains of bacteria.

The cloning of RM systems first began in the 1970's and since then those involved with the effort have had to contend with numerous problems. A problem inherent to every cloning project is identifying and isolating the gene(s) of interest. Some RM systems are plasmid borne so it has been relatively easy in these cases to isolate the DNA encoding both the methylase and endonuclease genes and transfer them onto a new vector (EcoRV: Bougueleret et al., Nucl. Acids Res. 12: 3659–3676, (1984); PaeR7: Theriault and Roy, Gene 19: 355–359, (1982); Gingeras and Brooks, Proc. Natl. Acad. Sci. USA 80: 402–406, (1983); PvuII: Blumenthal et al., J. Bacteriol. 164: 501–509, (1985)).

The large majority of RM systems, however, are not plasmid encoded. These have been cloned mainly by "shotgun" methods in which the chromosomal DNA is cleaved into small pieces of clonable size using restriction endonucleases or other means. The pieces are then ligated en masse onto a cloning vector and transformed into a suitable bacterial host generating "libraries" in which each gene is represented multiple times. The difficulty is then to find selective procedures to identify those clones carrying the genes of interest out of the thousands that have been generated.

The first selection method successfully used to clone RM systems, inspired by the classic properties of the systems, involved the use of bacteriophage: cells carrying an RM system survived when exposed to phage attack, while those not expressing the RM system did not (HhaII: Mann et al., Gene 3: 97–112, (1978); PstI: Walder et al., Proc. Natl. Acad Sci. USA 78: 1503–1507, (1981)). Unfortunately, this method had limited success. Cloned RM systems are not always expressed in a manner that confers selective survival. In addition, when there are multiple RM systems in a cell, one cannot target the particular RM system one wishes to clone. Furthermore, other cloned functions besides RM systems are able to protect the cells against phage attack and enable them to survive the selection (Mann et al. Ibid; Howard et al., Nucl. Acids Res. 14: 7939–7951, (1986); Slatko et al., Nucl. Acids Res. 15: 9781-9796, (1987)).

A second method, which has had more widespread success, selects for expression of the methylase gene: upon transformation, any plasmid within the library which contains and expresses the cloned methylase gene will methylate its cognate recognition sites. When the library is subsequently selected by cleavage with an endonuclease of the appropriate specificity, the modified plasmids should not be cut and remain viable upon a second transformation step. The other plasmids not containing the methylase gene should be cleaved by the endonuclease and therefore transform at a much-reduced efficiency (Kiss et al., Nucl. Acids Res. 13:6403-6421, (1985); Lunnen et al., Gene 74: 25-32, (1988)). In all RM systems thus far studied, the restriction endonuclease and modification methylase genes lie in close proximity to one another (Wilson, Nucl. Acids Res. 19: 2539-2566, (1991)); therefore, methylase selection often yields a complete RM system. In other cases the selection may yield only the methylase gene; however, it has often been possible to clone a larger or an adjacent fragment containing the endonuclease gene in a second step (see e.g. Kiss et al. Ibid).

In addition to finding a suitable selection procedure, a number of other difficulties have arisen when attempting to clone RM systems. For example, in some systems problems have arisen when the endonuclease gene is introduced into host cells not already protected by modification. If both genes are introduced together on a common DNA fragment the methylase may not adequately protect the host genome from the action of the endonuclease, if, for example, the endonuclease is produced too soon or in too large quantity. Methods have since been devised to clone the two genes separately on different vectors, in order to protect the cell against activity of the endonuclease gene before the latter is introduced (Howard et al. Ibid). The judicious selection of vectors can be essential to the stability of the clone as well as sufficient production of endonuclease (Brooks et al., Nucl. Acids Res. 19: 841-850, (1991)).

Yet another obstacle to cloning RM systems in *E. coli* manifested itself during the attempt to clone and express diverse methylases. *E. coli* has a number of systems that restrict foreign DNA containing heterologous cytosine and/or adenine methylation (Raleigh and Wilson, Proc. Natl. Acad. Sci. USA 83: 9070-9074, (1986); Noyer-Weidner et al., Mol. Gen. Genet. 205: 469-475, (1986); Waite-Rees et al., J. Bacteriol. 173: 5207-5219, (1991)). These systems became apparent only during attempts to clone a variety of methylase genes and establish them in genetically marked *E. coli* strains. The problem has been overcome in some cases by generating *E. coli* mutants deficient in these systems. Problems still persist in cloning RM systems; however, as more systems are studied, better cloning methods are being developed.

BglII, from the Gram-positive bacterium *Bacillus globigii*, was one of the first RM systems to be identified and characterized. (Wilson and Young, in Schlessinger (ed.), Microbiology-1976, American Society for Microbiology, p. 305-357, (1976)). As the name implies, there exists another RM system, BglI, isolated from the same species Both BglI and BglII systems behave in a classic manner, protecting the bacterium against infection by unmodified bacteriophages. Investigators found it very difficult to separate R.BglI from R.BglII by biochemical means since the enzymes have similar molecular weights and ionic properties (Pirrotta, Nucl. Acids Res. 3: 1747-1760, (1976)); therefore, genetic methods were employed. *B. globigii* was mutagenized by standard methods, and individual isolates were screened for reduced levels of phage restriction using unmodified phage propagated on *Bacillus subtilis*, a closely related strain. Two mutant strains, designated *B. globigii* RUB561 and RUB562, producing only R.BglI or R.BglII, respectively, were generated in this manner (Duncan et al., J. Bacteriol. 134: 338-344, (1978)). The mutant strains still maintained methylase functions for both BglI and BglII. The investigators thought the use of mutagenesis coupled with screening for phage restriction would be a generally applicable method for the separation and purification of RM system components. However, since then, the discovery of RM systems has far outpaced the development of genetic systems in diverse bacteria and the method has not been applied to other RM systems. Nonetheless, the two *B. globigii* strains have been used commercially to produce BglI and BglII endonucleases. In addition, both strains have proved essential in the cloning of the BglII RM system, as described below.

SUMMARY OF THE INVENTION

The present invention relates to recombinant DNA encoding the genes for the BglII restriction endonuclease and modification methylase obtainable from *Bacillus globigii* RUB562 (Duncan et al. Ibid; New England Biolabs Culture Collection) as well as related methods for production of the enzymes from cells containing the recombinant DNA. This invention also relates to a transformed host which expresses the restriction endonuclease BglII, an enzyme which recognizes the DNA sequence 5'-AGATCT-3' and cleaves within the recognition sequence between the A and G leaving a 4 base 5' extension (Pirrotta Ibid). BglII restriction endonuclease produced in accordance with the present invention is substantially pure and free of contaminants normally found in restriction endonucleases made by conventional techniques as described in step 19 of Example 1. One preferred method for cloning the BglII RM system comprises: constructing an appropriate vector, creating several libraries containing DNA from *B. globigii* RUB561($R_{II-}M_{II+}$), isolating those clones which contain DNA encoding the BglII modification methylase, purifying the BglII restriction endonuclease protein and determining its amino terminal sequence, designing a degenerate oligonucleotide probe specific for the 5' end of the endonuclease gene, locating the end and orientation of the endonuclease gene on the plasmid encoding the BglII methylase, comparing the restriction profile of the fragment encoding bglIIM from *B. globigii* RUB561 to the corresponding region of the *B. globigii* RUB562 ($R_{II+}M_{II+}$) chromosome, cloning the appropriate fragment from *B. globigii* RUB562, screening the resulting clones for endonuclease activity, cloning the endonuclease gene behind a regulated promoter, transforming the regulated endonuclease construct into a host carrying the BglII methylase gene on a medium copy number vector, growing the cells and inducing endonuclease expression under prescribed conditions, and purifying the BglII endonuclease using standard methodology.

DETAILED DESCRIPTION OF THE INVENTION

The present invention relates to recombinant DNA which encodes the BglII restriction endonuclease and modification methylase, as well as to the enzymes produced from a clone containing such recombinant DNA.

Figure 1:
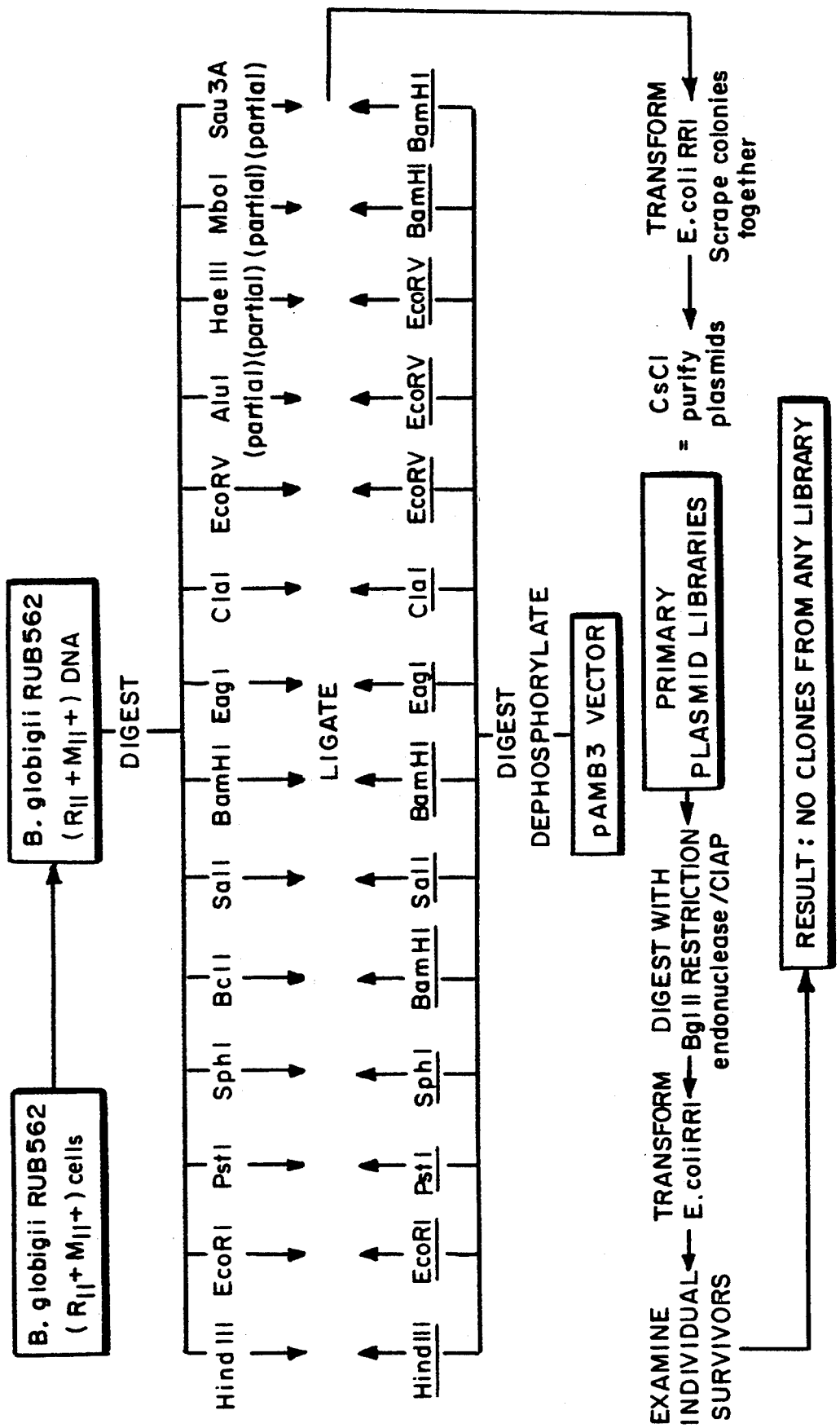
FIG. 1 illustrates attempts to clone the BglII RM system from *Bacillus globigii* RUB562 ($R_{II+}M_{II+}$). As shown, attempts to clone the complete system from this strain proved unsuccessful; therefore, they are not described in the text.
Figure 2A:
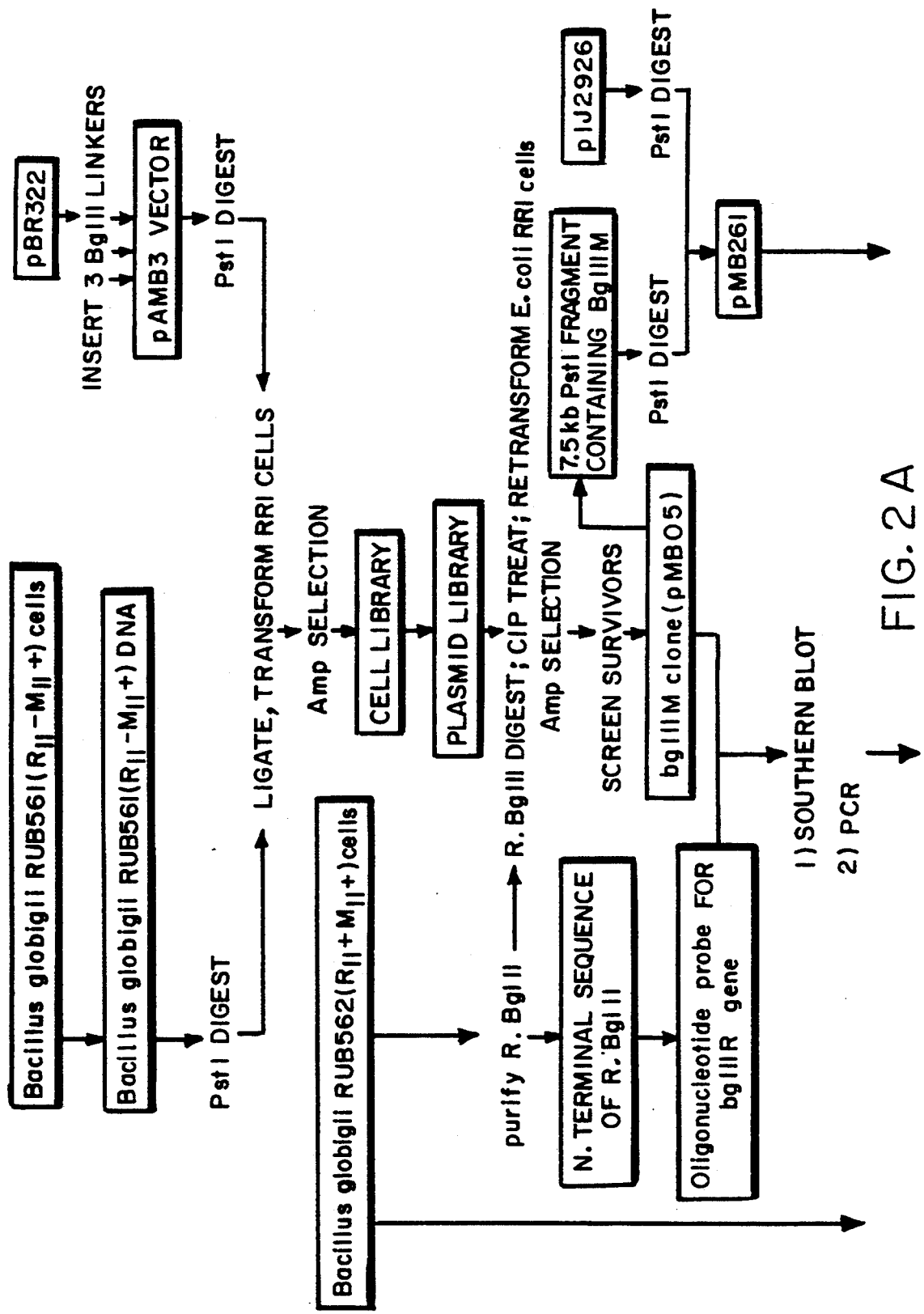
FIG. 2 illustrates the preferred method for cloning and producing BglII endonuclease, as described in the text.
Figure 2B:
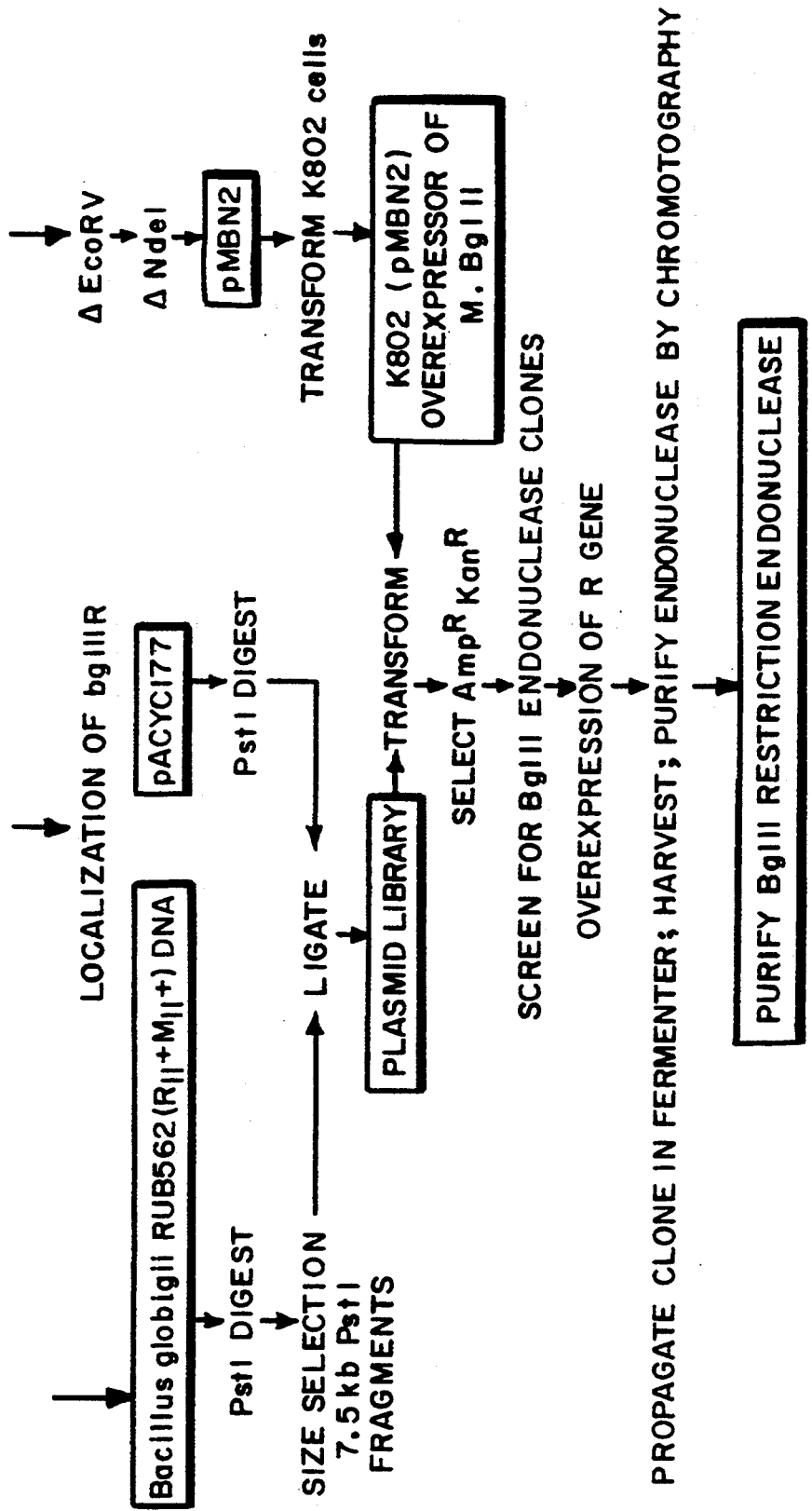

In accordance with the present invention, the cloning of the BglII RM system was complicated by several factors. First, none of the common cloning vectors (i.e. pBR322, pUC19, pACYC184, etc.) contained BglII sites; a new vector had to be engineered. Second, and more importantly, unlike many other RM systems that had been cloned, the two BglII RM genes cannot be transferred in a single step to a naive *E. coli* host. Attempts at making and selecting libraries in the traditional manner proved fruitless (see FIG. 1). Fortunately we had at our disposal a mutated *B. globigii* strain in which the BglII endonuclease gene (bglIIR) had been inactivated. With DNA isolated from the mutant strain, using our new vector with multiple BglII sites we were able to construct libraries, select for M.BglII expression and isolate a clone carrying the BglII methylase gene on a recombinant plasmid.

Cloning bglIIM from the mutant strain led to further complications in cloning bglIIR. Since it was impossible to clone the active bglIIR from the variant library, numerous additional steps proved necessary. These steps included the subcloning and overexpression of bglIIM on a higher copy vector, the preparation of an extremely pure sample of R.BglII from *B. globigii* RUB562; size determination of the endonuclease protein and sequence determination of its amino terminus, designing corresponding DNA oligonucleotide probes, and looking for the hybridization of the probes to the bglIIM recombinant plasmid. Furthermore, it was necessary to evaluate whether the mutant *B. globigii* RUB561 strain, from which the methylase gene had been cloned, contained any gross chromosomal rearrangements in the region of the endonuclease gene as a result of the mutagenesis procedure. After it had been determined that no rearrangements had occurred, the region containing the 5' end of bglIIR was mapped onto the bglIIM plasmid; a series of PCR experiments determined the orientation of the endonuclease gene. Using this information, a second genomic library was generated from size-selected restriction fragments of *B. globigii* RUB562 DNA cloned into pACYC177. The library was transformed into *E. coli* host cells protected by a bglIIM-containing plasmid. Transformant colonies were screened in groups of fifty for R.BglII activity; from these groups individual colonies carrying and expressing bglIIR were identified. It was then necessary to manipulate the clones further to generate an overexpressor of R.BglII.

The method described herein by which the bglIIM and bglIIR are preferably cloned and expressed is illustrated in FIG. 2 and includes the following steps:

1. Cloning vector construction: The plasmid pAMB3, a pBR322 derivative containing three strategically-placed BglII sites (FIG. 3), is constructed. Its construction is described in Example 1.
2. Genomic DNA purification: For the cloning of bglIIM, *Bacillus globigii* RUB561 is grown in LB medium. For the cloning of bglIIR, *Bacillus globigii* RUB562 is similarly grown. The cells are harvested and the DNA purified.
3. Genomic DNA digestion: *B. globigii* RUB561 DNA is digested to completion with a restriction endonuclease such as HindIII, EcoRI or PstI. Since PstI was the only digest to yield a bglIIM clone, only the details for this work will be described.
4. "Shotgun" library preparation: The digested genomic DNA is ligated to PstI-cleaved and dephosphorylated pAMB3 vector. The ligation mix is used to transform an *E. coli* host like RR1 or K802 (ATCC 31343 and ATCC 33526, respectively). RR1 is the preferred host strain. Electroporation is the preferred method of transformation, but chemical methods can be used.
5. Cell library selection: The transformation mixes are plated on selective antibiotic media; in this case tetracycline plates are used. After overnight incubation, transformants are scraped from plates and pooled to constitute the cell library. To ensure adequate representation of the *B. globigii* genome, only a library containing more than 10,000 colonies is used.
6. Recombinant plasmid purification: The recombinant plasmids are purified in toto from the cell library to form the plasmid library. Preferably the purification procedure includes cesium chloride-ethidium bromide gradient centrifugation.
7. Plasmid library selection: The plasmid library is then digested to completion with a large excess of R.BglII, prepared from *B. globigii*RUB562 cells. The endonucleolytic digestion will selectively cleave unmodified plasmids (not expressing bglIIM) which will increase the relative frequency in the population of intact bglIIM-carrying plasmids. The cleaved plasmids are then treated with a large excess of alkaline phosphatase, which also acts to decrease the transformation efficiency of plasmids not expressing bglIIM.
8. Identification of bglIIM clones: The digested plasmid library DNAs are electrophoretically transformed into a suitable host strain like RR1 or K802 and the transformants selected on antibiotic medium. DNA is isolated from individual colonies and analyzed for M.BglII-specific modification by resistance to cleavage by R.BglII. The plasmid DNA should be completely or substantially resistant to digestion. As a further confirmation, λ phage are grown on the putative bglIIM clone and the phage DNA purified and checked for R.BglII cleavage. Finally, the inserted region of the recombinant plasmid is deleted and the remaining vector retransformed, then purified and checked for the presence of intact BglII sites.
9. Mapping and subcloning bglIIM: Since the methylase gene is cloned from *B. globigii* RUB561, a mutant strain deficient in endonuclease activity, the methylase clones are not expected to and do not produce active R.BglII. It is necessary to clone bglIIR in a separate step from a second *B. globigii* strain (i.e. RUB562). Prior to cloning it is necessary to construct a host that produces M.BglII at a higher level. For this purpose bglIIM is located within the insert by deletion mapping combined with Tn5 transposon mutagenesis mapping. The fragment is transferred to pIJ2926, a pUC19 derivative with BglII sites within the multiple cloning site (Janssen and Bibb, Gene 124: 133–134, (1993)). By a series of deletion experiments, a subclone expressing a higher level of bglIIM is constructed (FIG. 4). The plasmid is designated pMBN2 (FIG. 4D).
10. Southern blot comparison of *B. globigii* RUB561 and RUB562 DNA: The 7.5 kb PstI fragment containing bglIIM from *B. globigii* RUB561 is hybridized in parallel to genomic DNA from *B. globigii* RUB561 and RUB562, respectively, to determine if gross chromosomal rearrangements in this area accompanied the mutagenesis of the RUB561 or RUB562 strains. No such rearrangements are found.
11. Locating bglIIR: R.BglII is purified from *B. globigii* RUB562 cells to near-homogeneity. The purified protein migrates as a single band of approximately 27 kDa on SDS polyacrylamide gels. It would therefore be encoded by a gene of approximately 750 bp.

The sequence of the first twenty-one amino acids is determined. A degenerate oligonucleotide probe, specific for the 5' end of the endonuclease gene, is synthesized and radioactively labeled for use in hybridization experiments. Hybridization experiments show bglIIR to lie at the end of the cloned PstI fragment proximal to bglIIM.

A polymerase chain reaction (PCR) experiment using sense and antisense bglIIR oligonucleotides, in conjunction with pBR322 specific primers, is used to determine the orientation of bglIIR. The PCR experiment shows the direction of bglIIR transcription to be toward bglIIM.

12. Cloning bglIIR: To circumvent the problems encountered in one-step cloning of the BglII RM system, bglIIR is cloned into modified host cells. Purified *B. globigii* RUB562 DNA is digested to completion by PstI endonuclease and appropriately sized fragments gel-purified and ligated to PstI-cut pACYC177. The ligation mixture is transformed by electroporation into *E. coli* cells carrying the plasmid pMBN2 expressing bglIIM; *E. coli* K802 is the host of choice. Transformants carrying both plasmids and thereby resistant to two antibiotics (i.e. ampicillin and kanamycin) are selected.

Figure 6A:
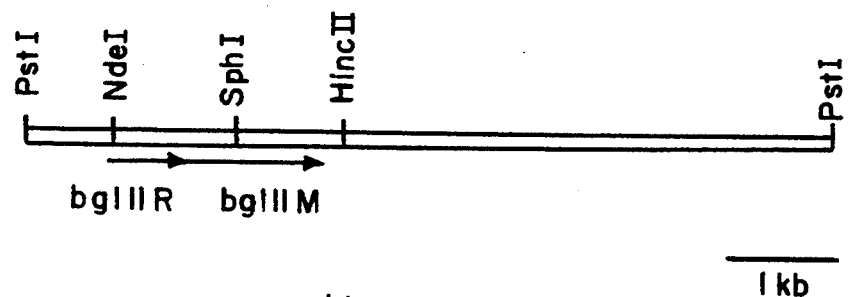
FIG. 6 schematically shows the process by which bglIIR was characterized, subcloned and overexpressed. In the diagram the thick hatched bar represents *B.globigii* RUB562 ($R_{II+}M_{II+}$) DNA containing the bglIIM and bglIIR genes. Important restriction sites are indicated. Position and orientation of bglIIR and bglIIM genes are indicated by long arrows. The promoters Plac and Ptac are indicated by short arrows. Plasmid vectors are shown in parentheses. Plasmid pAGR3 is described in FIG. 7. A. The 7.5 kb PstI fragment from *B. globigii* RUB562 containing bglIIM and bglIIR cloned into pACYC177 (Chang and Cohen, J. Bacteriol. 134: 1141–1156, (1978)) to form pMRB1. B. The 3.0 kb PstI-HincII region containing the complete BglII RM system whose nucleotide sequence was determined. C. The 2.0 kb PstI-SphI fragment, containing bglIIR, cloned into pUC18 to form pBglR1.8B. D. 800 bp fragment, produced by PCR, containing bglIIR. At the termini, BspHI and BamHI sites were engineered into the primers so that the fragment could be directionally cloned into the expression vector pAGR3 between the NcoI and BamHI sites. E. Fragment containing bglIIR as cloned into expression vector to form pAGRBglR2.

13. Identifying clones carrying bglIIR: Selected transformants are plated in duplicate in groups of fifty on antibiotic plates and screened for endonuclease activity. Colonies from one plate of each pair are pooled, lysed and the crude extracts assayed for R.BglII activity. For groups that test positive, individual colonies are grown and assayed separately for R.BglII activity. Plasmid DNA is purified from positive clones and inserted fragments analyzed to ascertain their identity. The pACYC177 plasmid containing the 7.5 kb PstI fragment encoding bglIIR and bglIIM is identified and designated pMRB1 (FIG. 6A).

14. Mapping and characterizing bglIIM and bglIIR genes: The complete BglII RM system is located on a 3.0 kb PstI-HincII subfragment of the original 7.5 kb PstI fragment by restriction mapping and subcloning FIG. 6B). Nucleotide sequence of the 3.0 kb subfragment is generated to aid in overexpression of the methylase and endonuclease genes.

Figures 4A, 4B, 4C, 4D, 4E, 4F, 4G:
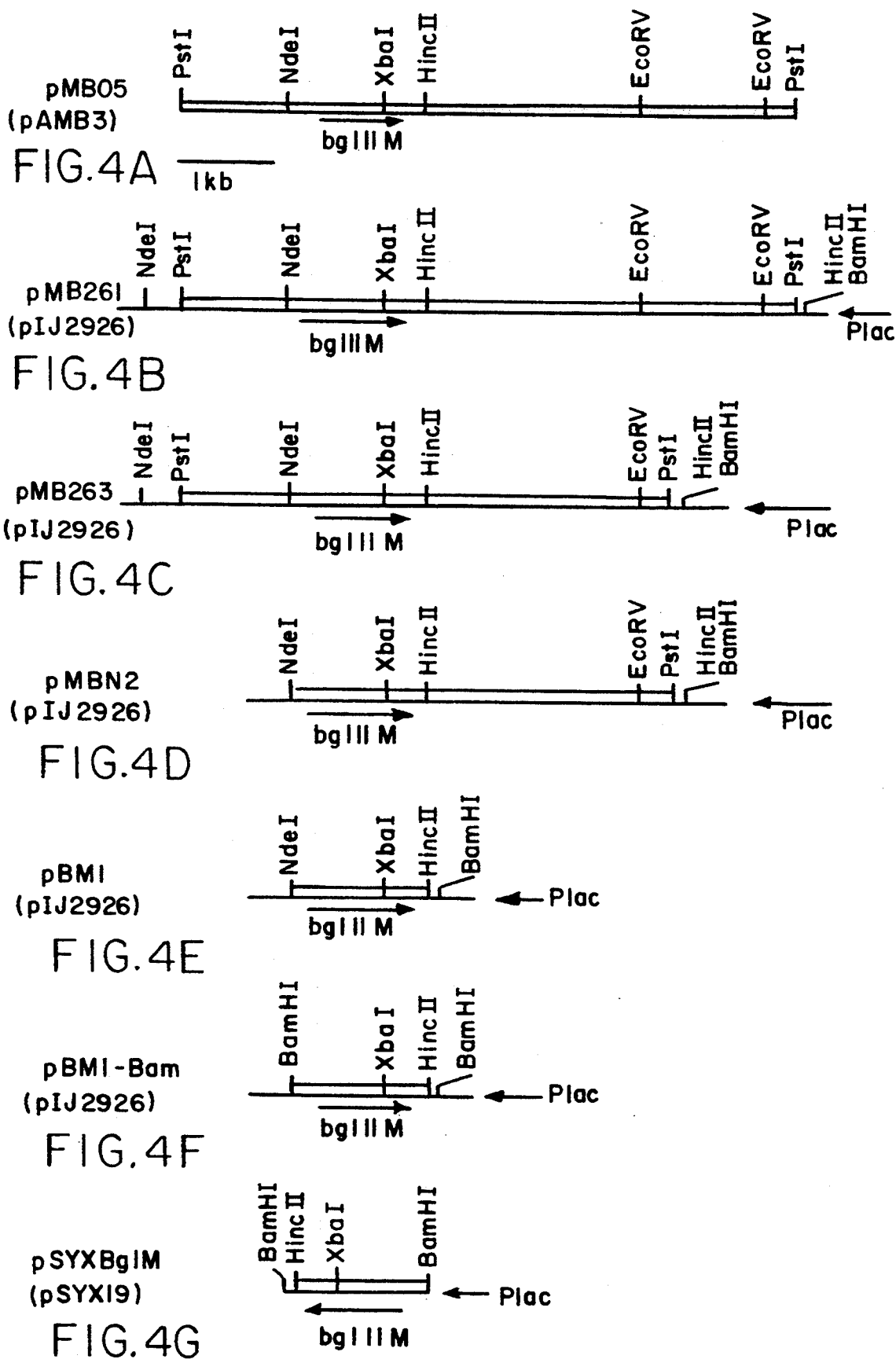
FIG. 4 is a schematic representation of the mapping and subcloning of the bglIIM gene. Within the diagram a thick hatched bar indicates the inserted *B. globigii* RUB561 ($R_{II-}M_{II+}$) DNA; plasmid vector DNA is indicated by a thin line. Position and orientation of bglIIM is shown by a long arrow; relative position and orientation of the lac promoter (Plac), when present, is shown by a short arrow. The plasmid vector used in each construction is shown on the left in parentheses. Details of vectors pAMB3 and pSYX19 are given in FIGS. 3 and 5, respectively. A. 7.5 kb PstI fragment of *Bacillus globigii* DNA carrying bglIIM, which was transferred onto pAMB3 to construct pMB05. Important restriction sites within the insert are indicated. B. PstI fragment transferred intact to the expression vector pIJ2926 to form pMB261. Relevant restriction sites within the vector are included. C. Insertion fragment of plasmid pMB263, formed by a 1.7 kb deletion between the EcoRV sites of pMB261. D. Insertion fragment of pMBN2, formed by NdeI deletion of plasmid pMB263. The deletion removed 1350 bp of insert DNA along with 220 bp of pIJ2926 vector. E. Insertion fragment of pBM1, formed by a 4.7 kb HincII deletion of pMBN2. F. Insertion fragment of pBM1-Bam, created by filling in the NdeI site with Klenow polymerase and adding a BamHI linker at that end. G. The 1.8 kb resultant BamHI fragment containing bglIIM which was inserted in vector pSYX19 to form pSYXBglM, the methylase construct used for the R.BglII overexpression clone.

15. Increasing expression of bglIIM: Preliminary experiments show that to overexpress bglIIR, it would first be necessary to increase bglIIM expression. The numerous attempts at bglIIM overexpression included moving bglIIM onto the *E. coli* chromosome behind a variety of strong *E. coli* promoters and substituting bglIIM with bstYIM from *Bacillus stearothermophilus* Y, whose product methylates sites including the BglII recognition sequence. Best results, however, are obtained by expressing bglIIM from the lac promoter on the medium copy number plasmid pSYX19, a derivative of pSC101 compatible with both pBR322- and pACYC-based plasmids (FIG. 5; S. Xu, New England Biolabs). The construct made is designated pSYXBglM (FIG. 4G).

Figure 7:
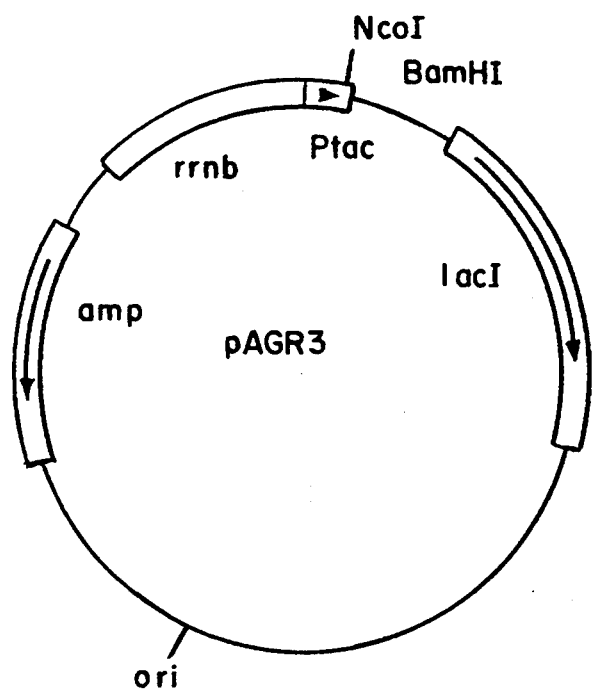
FIG. 7 is a schematic diagram of the plasmid vector pAGR3. The plasmid, constructed by W. Jack (New England Biolabs), is a derivative of pRS415 (Simons et al., Gene 53: 85–96, (1987)) into which has been added the lacI$^q$ repressor gene, a transcriptional terminator (rrnb), and the tac promoter (Ptac). Other features shown on the diagram are the origin of replication (ori), ampicillin resistance gene (amp), and the NcoI and BamHI cloning sites, which were used to insert bglIIR in the proper orientation. The translation initiation codon (ATG) is located within the NcoI site and is optimally situated behind the vector's ribosome binding site.
Figure 6B:
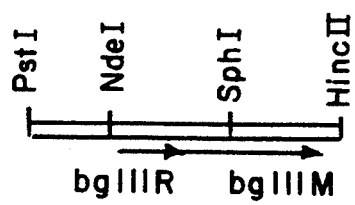
Figure 6C:
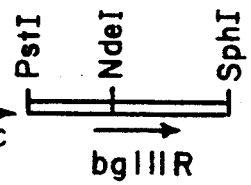
Figure 6D:
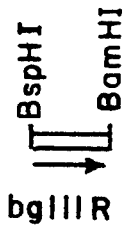
Figure 6E:
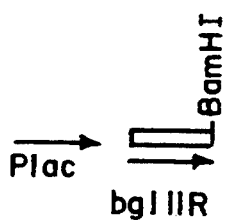

16. Overexpression of bglIIR: Attempts to optimize expression of bglIIR included using both constitutive and inducible strong promoters on plasmids of various copy number level. bglIIR proved unstable when cloned behind a strong constitutive promoter. Best results are obtained using the vector pAGR3, a pBR322 derivative with expression driven by the tac promoter, inducible by isopropyl-β-D-thiogalactopyranoside (IPTG) (FIG. 7; W. Jack, New England Biolabs). The bglIIR gene is transferred to pAGR3 and fused in-frame at the NcoI site to the tac promoter. This is accomplished by amplification of a DNA fragment containing bglIIR by PCR. Alternatively this construct can be and has been made by using site-directed mutagenesis instead of PCR. The endonuclease-expressing plasmid is designated pAGRBglR2 (FIG. 6E).

17. Construction of an overexpression strain: For overexpression, the *E. coli* strain ER2206 (E. Raleigh, New England Biolabs) is the preferred host. ER2206 is an overproducer of the lac repressor; a high concentration of lac repressor in the cell reduces expression from the tac promoter prior to induction. The plasmid pSYXBglM is transformed into the strain by electroporation, and transformants selected for kanamycin resistance.

In a second step, ER2206(pSYXBglM) is made competent, electrophoretically transformed with pAGRBglR2, and double transformants selected on antibiotic medium. Transformants are tested for R.BglII activity after growth in liquid culture to late-log phase, induction with IPTG for several hours, and preparation of crude extracts.

18. Production of R.BglII: R.BglII may be produced from ER2206 (pSYXBglM; pAGRBglR2) cells by propagation in a fermenter in a rich medium such as LB containing the appropriate antibiotics. Following induction with IPTG for several hours, the cells are harvested by centrifugation and disrupted by sonication, producing a crude cell extract containing R.BglII activity.

19. Purification of the R.BglII: R.BglII is purified from the crude cell extract described in step 18 by standard protein purification techniques such as ion exchange chromatography until the enzyme is substantially free of other contaminating endo- and exonucleases.

Although the above-outlined steps represent the preferred mode for practicing the present invention, it will be apparent to those skilled in the art that the above-described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE 1

Cloning of BglII Restriction Endonuclease and Modification Methylase Genes

[Note: Details of standard procedures used in Example 1 are included at the end of the section.]

1. Cloning vector construction: The cloning vector used was pAMB3, which was derived from pBR322 by insertion of 3 BglII linkers as follows:

10 μg of pBR322 was digested with 10 units of PvuII (endonucleases were from New England Biolabs and reactions were done under recommended conditions using the buffers supplied) in a reaction volume of 50 μl at 37° C. for 2 hrs. 10 μl of the reaction mix was then added to a 100 μl ligation reaction containing 2 μg nonphosphorylated BglII linker (dCAGATCTG; New England Biolabs), 40 units T4 DNA ligase (New England Biolabs), and 20 units SspI in the supplied ligase buffer (50 mM Tris pH 7.8, 10 mM MgCl$_2$, 10 mM DTT, 1 mM ATP, 25 μg/ml bovine serum albumin); the mixture was incubated overnight at room temperature, and then extracted once with an equal volume of chloroform. The ligation mixture was transformed into *E. coli* RR1 cells using the CaCl$_2$ method, and cells were plated on LB agar plates containing ampicillin (1 liter LB medium contains 10 g tryptone, 5 g yeast extract, 10 g NaCl, 1 g dextrose, 1 g MgCl$_2$, pH adjusted to 7.2 with NaOH. LB agar is LB medium with the addition of 1.5% agar). Plasmid DNA was isolated from individual transformants using the alkaline lysis miniprep method, digested with BglII and analyzed by electrophoresis on an agarose gel to screen for plasmids containing the linker. This construct was designated pB2066.

In a second round of experiments, a nonphosphorylated BglII linker was inserted at the SspI site of pB2066 by repetition of the method described above. This new construct, designated pAMB2, contained 2 BglII linkers.

In a separate experiment, 4 µg of pBR322 were digested with 40 units of DraI. After 30 min at 37° C., the reaction was terminated and the DNA purified using the phenol/chloroform extraction method. The resuspended DNA was ligated to an excess of BglII linker as described above, except that phosphorylated BglII linker (d(pCAGATCTG); New England Biolabs) was used and no restriction endonuclease was added to the ligation. After ligation for 2 hrs at 16° C., the reaction was extracted with phenol followed by chloroform, and precipitated with ethanol. The purified DNA was then digested with BglII to remove extra concatenated linkers. The endonuclease was heat killed, and the reaction religated at 16° C. for 1 hr. After chloroform extraction, the ligation mixture was used to transform *E. coli* RR1 cells using the CaCl$_2$ method, and the plated cells were selected for ampicillin-resistant colonies. Plasmids isolated from individual transformants by the alkaline lysis method were challenged with BglII and analyzed by agarose gel electrophoresis to screen for the proper construct. This construct, designated pB3232, has a BglII linker in place of the 19 bp DraI fragment outside the ampicillin resistance gene, but still has the DraI site within the ampicillin resistance gene, leaving the gene intact and functional.

Figure 3:
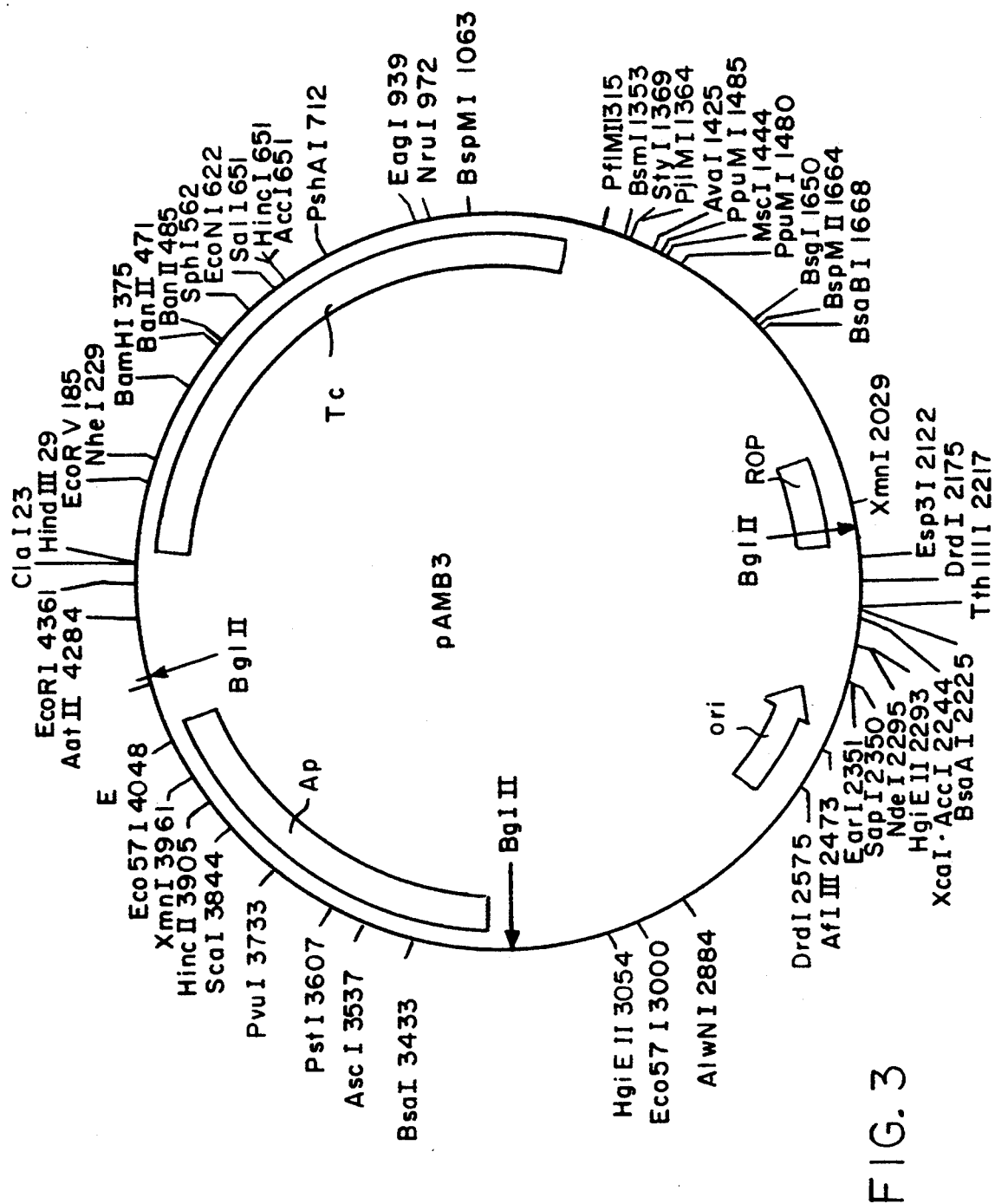
FIG. 3 is a schematic diagram of the vector pAMB3 used to make the *Bacillus globigii* genomic libraries. The vector is derived from pBR322; the figure is adapted from the New England Biolabs catalog map of that plasmid (1990–1991, p.110) and carries its numbering. The map shows the restriction sites of enzymes that cut pBR322 once or twice; the unique sites are shown in bold type. Ap=ampicillin resistance gene; Tc=tetracycline resistance gene; rop encodes a protein mediating the activity of RNaseI; ORI=origin of replication. The approximate locations of the 3 inserted BglII linkers are indicated by arrows.

The vector pAMB3 was created by combining pAMB2 and pB3232 in the following manner: 10 µg of pAMB2 was digested with 20 units each of PstI and NdeI in a single 150 µl reaction, and 10 µg of pB3232 was digested with 20 units each of PstI, NdeI, and BamHI in a parallel reaction. The digested DNAs were electrophoresed on a 0.7% agarose gel (IBI, molecular grade), and the desired 3051 bp PstI-NdeI fragment from pAMB2 and 1312 bp NdeI-PstI fragment from pB3232 isolated. 2 µg of each fragment were combined in a ligation mixture; after overnight ligation at room temperature and extraction with chloroform, the ligation mix was used to transform *E. coli* RR1 cells using the CaCl$_2$ method. Transformants were selected on LB agar plates containing both ampicillin and tetracycline, and plasmids from individual isolates digested with BglII and analyzed by electrophoresis to determine the proper construct. The pAMB3 plasmid is shown in FIG. 3.

2. Genomic DNA purification: DNA for methylase selection libraries was purified from *Bacillus globigii* strain RUB561. 10 ml of an overnight culture of *B. globigii* RUB561 was used to inoculate 500 ml LB medium and grown to saturation at 37° C. with shaking. Cells were harvested by centrifugation at 5000 rpm for 10 min in a Beckman J2-21 centrifuge with a JA-17 rotor; the cell pellets were washed by resuspension in a total of 100 ml Tris-EDTA buffer (100 mM Tris pH 8.0, 100 mM EDTA), and recentrifuged as before. The pellets were then resuspended in a total of 10 ml Tris-EDTA buffer and pooled; the centrifuge bottles were washed with an additional 10 ml Tris-EDTA buffer, and the wash added to the pool. Lysozyme (Sigma) was added to a final concentration of 0.125 mg/ml, the suspension mixed by gentle inversion, and the mixture incubated at 37° C. for at least 30 min. The suspension was then diluted with an equal volume of Tris-EDTA buffer at pH 9.0, SDS was added to a final concentration of 1%, and the suspension incubated at 50° C. for 15 min to complete the lysis.

Proteinase K (Boehringer Mannheim GmbH) was added to a final concentration of 0.05 mg/ml, and the incubation was continued at 37° C. for 1–2 hrs. The SDS was removed by dialysis against TE buffer (10mM Tris, pH8.0, 1 mM EDTA) and the dialysate was diluted with one volume of TE. Solid CsCl was added to 1 g/ml, and ethidium bromide to 100 µg/ml. The solution was subjected to ultracentrifugation in a Beckman Ti70 rotor at 44,000 rpm for 48 hrs, DNA bands were extracted with a syringe, and ethidium bromide was removed by extraction with isoamyl alcohol. CsCl was removed by dialysis as before, the dialysate was extracted with phenol followed by chloroform, and the solution was dialyzed a final time against TE as before. The final yield was 200 µg of *B. globigii* RUB561 DNA from 500 ml saturated culture.

3. Genomic and vector DNA digestion: In the course of attempting to clone the BglII RM system, libraries were made from numerous restriction digests. Since PstI was the only digest to yield a clone, only the details of this work will be described.

5 µg of *B. globigii* RUB561 DNA were cut to completion using an excess of PstI under standard conditions, and the reaction extracted once with phenol. DNA was precipitated by addition of two volumes of 95% ethanol.

5 µg of pAMB3 DNA were digested with PstI at 37° C. for 90 min. 22 units of calf intestinal phosphatase (Boehringer Mannheim GmbH) were added, and the reaction continued at 37° C. for an additional 30 min. The reaction was phenol extracted and ethanol precipitated in a similar manner to the *B. globigii* DNA.

4. DNA ligation: PstI-digested vector (pAMB3) and insert (*B. globigii* RUB561 chromosomal DNA) were ligated together in a 100 µl reaction containing 400 ng insert DNA, 100 ng vector DNA, and 20 units T4 DNA ligase in the recommended ligation buffer at room temperature overnight. The ligation mix was then dialyzed against H$_2$O on a Millipore VS filter for 30 min at room temperature; the filter was washed with an additional 100 µl H$_2$O and the wash combined with the ligation mix.

5. Primary cell library construction: *E. coli* RR1 cells were prepared for electroporation using the standard procedure. 5 µl of the dialyzed ligation mix from step 4 were electroporated into *E. coli* RR1 cells. The transformed cells were spread on large (150 mm) LB agar plates containing tetracycline. Following overnight incubation at 37° C., a total of approximately 12,000 transformants was obtained from 4 plates. The plates were overlaid with LB, and the colonies pooled to form the primary cell library.

6. Primary plasmid library isolation: Plasmids were isolated from the primary cell library using the standard Tritonlysis procedure. Following ultracentrifugation, the purified DNA was resuspended in a final volume of 1 ml TE, to a final concentration of approximately 0.1 mg/ml.
7. Selection of plasmid library: Approximately 2 μg of primary library DNA was challenged with 48 units of BglII endonuclease in a 100 μl reaction volume at 37° C.; after a 90 min digestion, 22 units calf intestinal phosphatase and an additional 32 units BglII were added, and incubation continued for another 60 min. DNA was purified as previously described and resuspended in 15 μl TE. The entire digestion and dephosphorylation reaction was then repeated on the resuspended DNA. The treated plasmid DNA was then dialyzed against H₂O as previously described.
8. Transformation: 5 μl of the dialyzed sample that had been diluted 1:100, containing approximately 5 ng DNA, were used to transform 40 μl E. coli RR1 cells by electroporation. The transformed cells were plated on LB agar plates containing tetracycline. Following overnight incubation at 37° C., an average of 8 transformants per plate were obtained from the 5 ng of selected library DNA, and about 8300 per plate with a comparable amount of unselected library DNA. The selection was therefore about 1000-fold.
9. Analysis of surviving plasmids: 16 of the transformants surviving selection were grown in liquid culture and their plasmid DNA isolated using the standard miniprep procedure. The plasmids were digested in parallel reactions with PstI and BglII respectively and analyzed by agarose gel electrophoresis. 15 of the 16 plasmids contained a 7.5 kb PstI insert and were completely resistant to BglII cleavage. The final plasmid contained no insert and was not resistant to BglII cleavage. One of the resistant clones was selected for further characterization and its plasmid designated pMB05 (FIG. 4A).

The 7.5 kb PstI insert believed to be carrying the bglIIM gene was removed from one of the BglII-resistant clones, and the vector religated to determine if its BglII sites were intact. Approximately 1 μg of the clone DNA was digested with 20 units PstI, and the vector religated overnight in a 1 ml volume. Approximately 0.5 μg of the DNA was then transformed into E. coli cells using the CaCl₂ method, and transformant DNA isolated by the alkaline lysis miniprep method. The plasmids were then digested in parallel reactions with PstI and BglII, as before, and analyzed by agarose gel electrophoresis. All plasmids tested had lost the 7.5 kb insert and were completely digested by BglII, confirming that it was a function encoded in the 7.5 kb insert that conferred resistance to BglII digestion.

10. Construction of a methylaseoproducing host: An extensive restriction map of pMB05 was made (FIG. 4A) and the approximate location of bglIIM determined by deletions and Tn5 insertion mutagenesis. In order to contruct a bglIIM clone with a higher level of methylase expression, the pMB05 insert was transferred to a high-copy pUC-derived vector and two regions of non-essential DNA were deleted from the insert.

20 μg of pMB05 DNA was digested with 80 units of PstI in a 500 μl volume for 3 hrs at 37° C. The digest fragments were separated by electrophoresis on a 0.7% agarose gel, and the 7.5 kb insert was isolated from the gel using the DEAE paper elution protocol. The isolated fragment was ligated to PstI-cleaved and dephosphorylated pIJ2926 vector DNA. The ligation mix was transformed into E. coli ED8767 cells (Raleigh et el., Nucl. Acids Res. 16: 1563–1575, (1988)) made competent by the RbCl method, plasmids were isolated using the alkaline lysis method, and the orientation of the insert within the vector was determined from restriction digests. This construct was designated pMB261 (FIG. 4B).

1 μg of pMB261 miniprep DNA was digested with 20 units of EcoRV in a 50 μl reaction. 12.5 μl of the 50 μl digest (containing 0.25 μg DNA) were diluted into a 600 μl ligation reaction. The ligation mixture was extracted once with phenol, once with chloroform, and DNA was precipitated by addition of 2 volumes of ethanol and freezing at −20° C. overnight. DNA was transformed into competent E. coli RR1 cells using the CaCl₂ method, and plasmids were isolated from 6 transformants and checked for the appropriate restriction pattern. The new construct was designated pMB263 (FIG. 4C).

4 μg of pMB263 miniprep DNA were digested to completion with NdeI in a 100 μl volume. After extraction with phenol and chloroform and precipitation with ethanol, 1 μg of the resuspended DNA was ligated in a 500 μl reaction overnight at room temperature. The ligation reaction was extracted once with chloroform and was used to transform E. coli ED8767 cells made competent using the CaCl₂ method. Plasmids from 9 transformants were isolated and checked for the appropriate restriction pattern. The new construct was designated pMBN2 (FIG. 4D).

E. coli K802 cells were made competent and electrophoretically transformed by pMBN2 using the standard procedure. Individual transformant colonies were selected for ampicillin resistance, the plasmids isolated by miniprep procedure and their restriction profiles checked. E. coli K802(pMBN2) was then used as host for cloning the endonuclease gene.

11. Purification and analysis of B. globigii RUB562 DNA: DNA from B. globigii RUB562 was purified in the same manner as RUB561 DNA, described in step 2.

Southern blot hybridization analysis (Maniatis et al., Molecular Cloning: A Laboratory Manual, Cold Spring Harbor, N.Y. (1982)) revealed no gross chromosomal differences between the strains RUB561 and RUB562 in the region surrounding bglIIM.

12. Location of bglIIR: The location and orientation of bglIIR were determined using degenerate oligonucleotide probes derived from the amino-terminal sequence of the endonuclease protein.

For this purpose, BglII endonuclease was purified to near-homogeneity from B. globigii RUB562 cells using standard protein purification techniques. Protein sequence of the first 16 amino acid residues of the purified protein was determined by sequential degradation with an Applied Biosystems 470A gas-phase sequenator, and was determined to be: Met Lys Ile Asp Ile Thr Asp Tyr Asn His Ala Asp Glu Ile Leu Asn (SEQ ID NO. 1). Based on the protein sequence, a 21-base antisense oligonucleotide probe of complexity 256: (ATYTCRTCNGCRTGRTCRTAR; SEQ ID NO. 2) and a 17-base sense probe of complexity 36: (ATGAARATHGAYATHAC; SEQ ID NO. 3), where R=A or G, Y=C or T, H=A or C or T, N=A or C or G or T, were synthesized.

Using Southern blot hybridization analysis of pMB05 plasmid with these degenerate endonuclease-specific hybridization probes (Howard et al. Ibid), the 5' end of the endonuclease gene was located on a 1.1 kb PstI-NdeI fragment within the pMB05 insert. In addition, a PCR experiment using the sense and antisense primers shown above in conjunction with pBR322 PstI clockwise and counterclockwise primers was performed on pMB05 to determine the orientation of bglIIR. Results of this experiment showed unambiguously that bglIIR was located and oriented such that the cloned PstI fragment should contain the entire gene.

13. Cloning bglIIR: bglIIR was cloned from a plasmid library of 7.5 kb size-selected *B. globigii* RUB562 DNA PstI fragments in pACYC177.

25 μg of *B. globigii* RUB562 genomic DNA were digested with PstI in a 400 μl volume at 37° C. for 4.5 hours. The digested DNA was separated by electrophoresis on a 0.7% agarose gel, and fragments sized approximately 6.5 to 8.5 kb were isolated using DEAE paper elution. The size-selected DNA was resuspended in 15 μl TE (to a final concentration of approximately 80 μg/ml).

5 μg of pACYC177 vector DNA were digested with PstI at 37° C. for 1.5 hours. Calf intestinal phosphatase and additional PstI were added at this point and the incubation continued an additional 60 min. Digested DNA was purified and resuspended in 20 μl TE.

Approximately 0.6 μg of size-selected RUB562 PstI fragments were ligated to 0.2 μg of PstI-digested and dephosphorylated pACYC177 with 400 units of T4 DNA ligase in a 53 μl reaction volume. 50 ng of the ligation mix were used to transform competent *E. coli* K802(pMBN2) using the CaCl$_2$ method. Transformants were selected for both carbenicillin and kanamycin resistances.

14. Identification of endonuclease-producing clones: From the transformants of the size-selected library, 11 sets of 50 colonies were picked in duplicate onto LB agar plates supplemented with carbenicillin and kanamycin. From one plate of each set, colonies were collected in 5 ml LB, pooled, harvested by centrifugation, and resuspended in 0.8 ml sonication buffer (100 mM NaCl, 50 mM Tris pH 8.0, 10 mM β-mercaptoethanol). 10 μl of 0.5M EDTA and 25 μl of 10 mg/ml lysozyme were added to each tube of cells, and the tubes were frozen at −70° C. After thawing, the cell extract was sonicated 15 sec in a Heat Systems W-225R sonicator (Ultrasonics, Inc.) and centrifuged for 10 min to remove cell debris. 1 μl and 7 μl respectively of each crude extract were assayed for R.BglII activity on BamHI-linearized pBR3232 DNA, which contains a single BglII site, in the recommended buffer for BglII, at 37° C. for 1 hr. R.BglII activity was observed in 9 of the 11 pools of crude extracts assayed.

Individual colonies from one of the positive plates were grown overnight in 5 ml LB supplemented with carbenicillin and kanamycin, and extracts were prepared and assayed for R.BglII activity as described above. 2 of the 11 crude extracts assayed displayed R.BglII activity. Further experiments showed both clones to express approximately 100,000 units of R.BglII activity per gram of cells, an overexpression of approximately threefold over *B. globigii* RUB562 cells.

The piACYC177 plasmid containing bglIIR and bglIIM was designated pMRB1 (FIG. 6A).

15. Nucleotide sequence determination of bglIIM and bglIIR: Using standard restriction mapping techniques, bglIIR and bglIIM were mapped to a 3.0 kb PstI-HincII fragment (FIG. 6B). The region was subcloned in several pieces by standard methods and the nucleotide sequence was generated for the entire region by the dideoxy method (Sanger et al., Proc. Natl. Acad. Sci. USA 74: 5463-5467, (1977); Sanger and Coulson, FEBS Letters 87: 107-110, (1978)) using DNA polymerase I Klenow fragment (New England Biolabs) and/or by the CircumVent sequencing method (New England Biolabs). The nucleotide sequence of a 3188 bp region encoding bglIIM and bglIIR is given in SEQ ID NO: 4.

Figure 5:
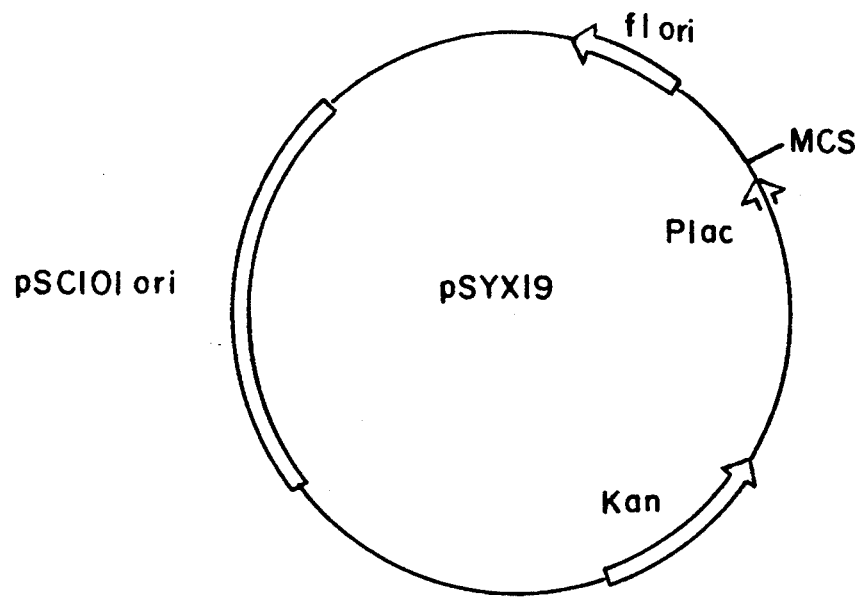
FIG. 5 is a schematic diagram of the plasmid vector pSYX19. The plasmid, a derivative of pWSK129 (Wang and Kushner, Gene 100: 195–199, (1991)), contains a mutation in its origin of replication (pSC101 ori) increasing its copy number. Also shown in the diagram: fl ori=fl origin of replication; Kan=kanamycin resistance gene; MCS=multiple cloning site; and Plac=lac promoter, whose position and orientation is indicated by a short arrow. The BamHI site, into which bglIIM is inserted, is located in the MCS.

16. Preparation of an overexpressing methyklase construct: To increase its expression bglIIM was cloned onto pSYX19 (FIG. 5).

1.6 μg of pSYX19 were digested with 60 units of BamHI in a total volume of 50 μl. Digestion was carried out at 37° C. for 90 min. 10 units calf intestinal phosphatase were added, and the reaction was incubated an additional 30 min at 37° C. The digested DNA was purified and resuspended in 10 μl TE.

1 μg pMBN2 was digested with 30 units of HincII in a total volume of 50 μl at 37° C. for 1 hr. The digested DNA was purified as described previously, resuspended in 10 μl TE, and religated with 400 units of T4 DNA ligase in a total volume of 50 μl. Ligation was carried out at 16° C. overnight. *E. coli* ED8767 cells were electroporated with 2 ng of the ligated DNA and the cells plated on LB agar plates containing carbenicillin. Plasmids were isolated from transformants using the alkaline lysis miniprep method, digested in tandem reactions with NdeI first and then HincII, and analyzed by electrophoresis on an agarose gel. Plasmid from one of the transformants with the desired HincII deletion was purified using the Triton lysis method and called pBM1 (FIG. 4E).

5 μg of pBM1 was digested with 60 units of NdeI in a total volume of 50 μl at 37° C. for 1 hr. The digested DNA was purified as described previously and resuspended in 20 μl TE. The resuspended DNA was treated in a 50 μl reaction volume with 10 units of DNA polymerase I Klenow fragment and 0.3 mM each of dATP, dCTP, dGTP, and dTTP in the recommended buffer, to fill in the ends. The reaction was incubated at 25° C. for 30 min, and then at 65° C. for 5 min. 10 μl of this reaction were added to a 100 μl ligation reaction containing 1 μg phosphorylated BamHI linker (d(pCGGATCCG); New England Biolabs) and 1200 units of T4 DNA ligase. Ligation was carried out at 16° C. overnight. *E. coli* ED8767 cells were electroporated with approximately 5 ng of the ligated DNA and cells plated on LB agar containing carbenicillin. Plasmids were isolated from transformants using the alkaline lysis miniprep method, digested with BamHI, and analyzed by electrophoresis on an agarose gel. Plasmid from one of the transformants with the desired BamHI linker was isolated using the Triton lysis method and called pBM1-Bam (FIG. 4F).

10 μg of pBM1-Bam were digested with 160 units of BamHI in a total volume of 150 μl. Digestion was carried out at 37° C. for 60 min. The fragments of digested plasmid were separated by electrophoresis on a 0.5% agarose gel. The 1.8 kb DNA band was excised, and DNA was purified using the Prep-a-Gene DNA Purification Matrix Kit (Bio-Rad Laboratories) according to manufacturer's specifications. DNA was resuspended in a final volume of 75 μl in Prep-a-Gene Elution Buffer.

0.1 μg of BamHI-digested pSYX19 was ligated to 0.75 μg bglIIM fragment with 400 units T4 DNA ligase in a 50 μl reaction volume for 18 hours at 16° C. The ligation was stopped by extracting once with an equal volume of chloroform, and was dialyzed against H$_2$O.

E. coli ED8767 cells were electroporated with 10 μl of the ligation mixture, and cells were plated on LB agar containing kanamycin. Following overnight incubation at 37° C., 12 of the transformants obtained were grown up in 5 ml cultures of LB broth containing kanamycin, and their plasmid DNA was isolated using the alkaline lysis miniprep procedure. Plasmid DNA was checked for proper restriction fragments; one colony was also tested for ability to methylate λvir phage (New England Biolabs Culture Collection) DNA in vivo. This new construct was designated pSYXBglM (FIG. 4G).

17. preparation of an inducible endonuclease construct: To overexpress the endonuclease gene, the expression vector pAGR3 (FIG. 7) was employed. bglIIR was amplified by PCR from an existing clone called pBglR1.8B (FIG. 6C). BspHI and BamHI sites were created within the oligonucleotide primers used in the reaction. Primer 1 contains sequence including the translational start of bglIIR, and has altered 2 bases of the original sequence to create the underlined BspHI site: 5' GGA GAC ACT CTC A TG AAG ATT G 3' (SEQ ID NO. 5). Primer 2 contains sequence from just beyond the stop codon of bglIIR, and has altered 2 bases of the original sequence to create the underlined BamHi site: 5' TGT TTA TAT GGA TCC TCA CTC AC 3' (SEQ ID NO. 6). The 0.8 kb fragment between these two primers was amplified in a PCR reaction with 2.5 units Taq DNA polymerase (Bethesda Research Laboratories), 10 ng pBglR1.8B template, and 0.25 mM each primer in (16.6 mM (NH$_4$)$_2$SO$_4$, 67 mM Tris-HCl pH 8.8, 6.7 mM MgCl$_2$, 10 mM β-mercaptoethanol, 187 μM each dNTP, 100 μg/ml BSA) at 93° C. for 1.5 min, 60° C. for 1.5 min, and 72° C. for 1.5 min, for 30 cycles. The sample was also incubated at 93° C. for 5 min prior to the first cycle, and at 72° C. for 3 min following the final cycle.

The PCR product was then purified for digestion by extraction once each with phenol and then chloroform, precipitated with ethanol in a dry ice-ethanol bath for 12 min, collected by centrifugation, and resuspended in 10 μl TE. The resuspended DNA (approximately 3 μg) was then digested with 50 units BamHI and 12.5 units BspHI in a 50 μl reaction volume at 37° C. for 60 min. The digested DNA was separated by electrophoresis on a 0.7% agarose gel, the proper band excised, and the DNA purified using the Bio-Rad Prep-a-Gene kit according to manufacturer's instructions and resuspended in 30 μl Prep-a-Gene Elution Buffer.

The digested PCR product was ligated to NcoI-and BamHI-digested and dephosphorylated pAGR3 DNA, and the ligation mixture electroporated into E. coli ER2206 cells containing the pSYXBglM plasmid. Transformed cells were selected on LB agar plates containing carbenicillin, kanamycin, and tetracycline. Plasmids were isolated using the alkaline lysis method, digested with restriction endonucleases, and analyzed using agarose gel electrophoresis. Clones containing plasmids with the proper configuration were tested for endonucleolytic activity in the crude extract. The new endonuclease-expressing plasmid was designated pAGRBglR2 (FIG. 6E).

Figure 8:
FIG. 8 is a photograph of an agarose gel illustrating the titration of BglII restriction endonuclease activity obtained from cell extracts of NEB#731. The numbering of the lanes on the gel is from left to right with lane 1 on the left and lane 8 on the right. The crude cell extract made from NEB#731 was diluted 1:100 and 1:1000, respectively, in Dilution Buffer (50 mM Tris, pH8.0, 100 mM NaCl). One $\mu$l and 5 $\mu$l from each dilution were used to digest 0.5 $\mu$g of pIJ2926 DNA in a 50 $\mu$l reaction mix containing 10 mM Tris, pH8.0, 10 mM MgCl$_2$, 100 mM NaCl, and 10 units SspI. After incubation at 37° C. for 30 min, 30 $\mu$l of reaction mix from each dilution is loaded onto a 0.7% TBE agarose gel which is run for 1 hr and then photographed. Included in the lanes on the gel are: λDNA cut with BstEII as molecular weight markers (lanes 1 and 8); reaction mix containing 16 units purified BglII (positive control; lane 2); reaction mix containing 0.05 $\mu$l crude extract (lane 3); reaction mix containing 0.01 $\mu$l crude extract (lane 4); reaction mix containing 0.005 $\mu$l crude extract (lane 5); reaction mix containing 0.001 $\mu$l crude extract (lane 6); reaction mix containing no BglII (negative control; lane 7).

The new clone was tested for optimal growth and expression conditions. Best results were obtained when the clone was grown in LB containing carbenicillin, kanamycin, and tetracycline at 30° C. to late-log phase (a reading of 100 on a Klett-Summerson photoelectric colorimeter), induced with 0.5 mM IPTG, and grown an additional 20 hrs at 30° C. before harvest. Under these conditions, the yield of R.BglII was approximately 1,200,000 units per gram of cells, an overexpression of 40-fold over B. globigii RUB562 cells. An isolate of the clone selected for further characterization and optimization was given a strain designation of NEB#731. A sample of NEB#731 was deposited at The American Type Culture Collection at Rockville, Md. on Feb. 23, 1993 and given the Accession No. 69247. A titration of the BglII restriction endonuclease activity produced from crude cell extracts of NEB#731 is shown in FIG. 8.

18. Fermentation: A single colony was used to inoculate 1 liter of LB containing appropriate antibiotics, and the culture grown at 30° C. overnight to a final density of 10$^9$ cells/mi. The overnight culture was used to inoculate a fermenter with 100 liters of the same media at pH 7.1. The fermenter culture was grown at 30° C. to Klett=100, induced with 0.3 mM IPTG, and grown overnight at 30° C. Cells were harvested continuously in a Sharples centrifuge at 16,000 rpm. The final yield was 758 grams of cells.

19. R.BglII purification: Approximately 400 grams of cells were resuspended in approximately 1200 mls of buffer A (20 mM Tris-HCl pH 7.1, 0.1 mM EDTA, 10 mM β-mercaptoethanol) containing 50 mM NaCl, and broken with a Manton-Gaulin 15M lab homogenizer (about 4 passes at 12,000 psi or until OD$_{595}$ and OD$_{260}$ leveled off). Debris was removed by centrifugation in a Sharples centrifuge for 40 min. Solid NaCl was added to the supernatant to a final concentration of 400 mM and polyethylene glycol (PEG) to 7.5% (added over a 30 min period, with stirring). The PEG was precipitated by spinning in a Beckman centrifuge at 4000 rpm for 20 min and the pellet discarded.

The supernatant was diluted with buffer A to a final concentration of 150 mM NaCl, monitored with a conductivity meter. The sample was applied to a 5 cm×13 cm heparinsepharose column (Pharmacia LKB Biotechnologies) equilibrated with buffer A containing 150 mM NaCl. The column was washed with approximately 500 ml of buffer A containing 150 mM NaCl. Protein was eluted with a 2000 ml gradient of 150 mM to 1200 mM NaCl in buffer A, and 24 ml fractions were collected. R.BglII activity eluted between 0.6 and 0.85M NaCl. At this point and throughout the purification, activity was measured by an assay using 1 μl λDNA (New England Biolabs) as substrate, 1 μl column fractions, and standard buffer conditions, incubated at 37° C. for 2 min.

Active fractions were pooled and dialyzed overnight vs. 4 liters buffer A containing 150 mM NaCl. The dialysate was applied to a second heparin-sepharose column (Pharmacia LKB), 1.5 cm×34 cm, equilibrated with buffer A with 150 mM NaCl. The column was washed with 2 column volumes of buffer A containing 150 mM NaCl. Protein was eluted with a 1000 ml gradient of 150 mM to 1200 mM NaCl in buffer A, and 12 ml fractions were collected. R.BglII endonuclease activity, assayed as above, eluted between 0.4 and 0.65M NaCl.

Active fractions were pooled, bovine serum albumin was added to a final concentration of 100 μg/ml, and the solution dialyzed overnight vs. storage buffer (50 mM KCl, 10 mM Tris pH 7.4, 0.1 mM EDTA, 1 mM DTT, 50% glycerol) to reduce the volume.

The dialysate was applied to a Sepadex G-75 sizing column (2.5 cm × 114 cm) and the column run with buffer B (50 mM KCl, 10 mM Tris pH 7.4, 0.1 mM EDTA, 1 mM DTT, 10% glycerol) at a flow rate of 4.5 ml/hr. R.BglII eluted in a volume of 60 ml; active fractions were pooled, bovine serum albumin added to a final concentration of 200 mg/ml and the enzyme redialyzed into storage buffer.

Using this purification regimen, $1.2 \times 10^6$ units of R.BglII was produced, a 16% yield.

The BglII restriction endonuclease obtained from this purification was substantially pure and free of nonspecific endonuclease and exonuclease. The purity of the BglII restriction endonuclease preparation was checked by looking at the following criteria: 1) Ligation: After a 15-fold overdigestion of λDNA, greater than 95% of the DNA fragments produced could be religated with T4 DNA Ligase (at a 5' termini concentration of 1-2 mM at 16° C.). Of these ligated fragments, 95% were able to be recut. 2) Prolonged digestion: After incubating a 50 μl reaction containing 1 μg of λDNA and 400 units of enzyme for 16 hours, the same pattern of bands was produced as with a reaction containing 1 unit of enzyme incubated for 1 hour. 3) Exonuclease activity: After incubation of 3,000 units of enzyme for 4 hours at 37° C. in a 50 μl reaction containing 1 μg sonicated [$^3$HI DNA ($10^5$ cpm/mg), less than 0.1% of the radioactivity was released. 4) Endonuclease contamination: After incubation of 80 units of enzyme for 4 hours at 37° C. in a 50 μl reaction containing 1 μg φX174 RFI DNA, 10% of the DNA was converted to RFII. All tests were performed in the following reaction buffer: 50 mM NaCl, 10 mM Tris-HCl, 10 mM MgCl$_2$, 1 mM DTT (pH 7.9 at 25° C.).

DETAILS OF STANDARD PROCEDURES

1. Antibiotic additions to media: To both liquid media and agar plates the following antibiotics at the stated concentrations were added as needed: ampicillin (50 μg/ml); carbenicillin (50 μg/ml); tetracycline (10 μg/ml); kanamycin (50 μg/ml).
2. DNA purification following restriction endonuclease digestion: The restriction digestion reaction is extracted once with an equal volume of phenol and once with an equal volume of chloroform. Two volumes of 95% ethanol are then added and the mixture incubated 10 min in a dry ice-ethanol bath to precipitate the DNA. The DNA is collected by centrifugation in an Eppendorf microcentrifuge at 4° C. for 10 min, the supernalant is decanted, and the DNA pellet resuspended in an appropriate volume of TE buffer.
3. Preparation of competent E. coli cells using CaCl$_2$: E. coli cells are prepared for transformation by growing in liquid culture to late-log phase (Klett=100) and harvesting by centrifugation. Cells are washed in half volume 50 mM CaCl$_2$, harvested as before, and finally resuspended in 1/50 original volume 50 mM CaCl$_2$.
4. Tranformation of competent calcium-treated E. coli cells: Cells are transformed by mixing DNA with 200 μl cells and incubating 20 min on ice. Cells are heat shocked by incubation for 2 min at 42° C. 1 ml of LB medium is added, cells are incubated 1 hr at 37° C. and spread on agar plates containing the appropriate antibiotic(s).
5. Plasmid isolation by alkaline lysis "miniprep" method: Cells from a 5 ml overnight culture are harvested by centrifugation in a Beckman JA-17 rotor at 5000 rpm for 10 min and resuspended in 100 μl ice-cold GET buffer (50 mM glucose, 10 mM EDTA, 25 mM Tris-HCl pH 8.0, 4 mg/ml lysozyme). Following incubation for 5 min at room temperature, 200 μl of a freshly-prepared solution of (0.2N NaOH, 1% SDS) is added. The solution is gently mixed by inversion and incubated 5 min on ice. To the lysate is added 150 μl of a 5M potassium acetate solution adjusted to pH 4.8 with glacial acetic acid. The cell lysate is mixed, incubated 5 min on ice, and centrifuged for 5 min in an Eppendorf centrifuge at 4° C. The supernatant is extracted once with an equal volume of phenol:chloroform 1:1, mixed, and spun for 2 min in an Eppendorf centrifuge. Two volumes of 95% ethanol are added to the top layer, the mixture is incubated 5 rain at room temperature, and the DNA is collected by centrifugation for 5 min in an Eppendorf centrifuge. The pellet is washed with 1 ml 70% ethanol and recentrifuged as before. The supernatant is decanted, the DNA pellet allowed to air-dry or dried in a vacuum desiccator, and the dry pellet resuspended in 50 μl TE containing 20 μg/ml RNase.
6. Transformation of E. coli cells by electroporation: 1 liter of LB medium is inoculated 1:500 with an overnight culture of E. coli cells. When the culture reaches mid-log phase (Klett=65), the cells are harvested by centrifugation at 4000 rpm for 15 min in a Beckman J2-21 centrifuge with a JA-14 rotor. The supernatant is decanted and the cells resuspended in 1 liter sterile H$_2$O at 4° C. Cells are harvested as above and resuspended again in 0.5 liter sterile H$_2$O at 4° C. Cells are harvested as above and resuspended a third time in 20 ml sterile H$_2$O containing 10% glycerol at 4° C. Cells are harvested as above and resuspended a final time in 2 ml sterile H$_2$O containing 10% glycerol at 4° C. Cell density by this point should be at least $3 \times 10^{10}$ cells/ml. Cells prepared as such can be used immediately or stored at −70° C. indefinitely and thawed on ice immediately before use.

Cells are electroporated by mixing DNA (1–40 ml volume) with 40 μl cells and incubating 1 min on ice. Current is applied to the mixture with a Bio-Rad Gene Pulser apparatus set to 25 μFD capacitance and 200 Ω resistance with a 2.5 kV pulse. The electroporated cells are resuspended in 1 ml LB and incubated at 37° C. for 1 hr before spreading on agar plates containing the appropriate antibiotics.

7. Procedure for plasmid isolation by Triton lysis: Cells are harvested from liquid culture by centrifugation at 5000 rpm for 15 min in a Beckman J2-21 centrifuge with JA-17 rotor, and resuspended in 8 ml Tris-sucrose buffer (50 mM Tris pH 8.0, 25% sucrose) per liter of culture. The cells are then pooled; to the pool is added 0.8 ml 0.5M EDTA pH 8.0, 0.8 ml 10 mg/ml lysozyme, and 5.6 ml Triton Buffer (62.5 mM EDTA, 1% Triton X-100, 50 mM Tris-Cl pH 8.0) per liter of culture. The components are mixed by gentle inversion, incubated on ice for 30 min, and centrifuged at 16,000 rpm for 45 min in the same rotor as above to remove cell debris. 1.1 g/ml CsCl is added to the supernalant, followed by ethidium bromide to 100 μg/ml. The mixture is spun at 44,000 rpm for 48 hours (or 55,000 rpm for 24 hours followed by 44,000 rpm for 1 hour) in a Beckman L8-55 ultracentrifuge with a Ti70 rotor. Following centrifugation, DNA bands are removed by syringe from the CsCl gradients, diluted with 2 volumes of $H_2O$, and DNA precipitated from the resulting solution by addition of 2 volumes 95% ethanol and freezing at $-20°$ C. for at least 30 min. The DNA is collected by spinning at 12,000 rpm for 20 min in a Beckman J2-21 centrifuge with a JA-17 rotor, the supernatant decanted, and the pellet resuspended in 1-2 ml TE. The DNA solution is extracted once with an equal volume of phenol, followed by extraction with an equal volume of chloroform. LiCl is added to a concentration of 0.2M, and then 2 volumes of 95% ethanol are added. DNA is precipitated a second time by freezing at $-70°$ C. overnight, and then collected as before. The final DNA pellet is resuspended in 0.5 ml TE.

8. Paper elution of DNA from agarose: Whatman Chromatography paper DE81 is soaked for several hours in 2.5M NaCl, gently washed for several minutes with $H_2O$, and allowed to dry.

Following separation of the fragments by agarose gel electrophoresis, a well is cut into the gel next to the DNA band to be purified, and DEAE paper prepared as above is inserted into the well. The well is filled with buffer, and the gel is turned at a 90° angle such that the band of interest will migrate into the cut well and run unsubmerged until it has done so.

The wash apparatus consists of a 0.5 ml Eppendorf tube with a hole in the bottom placed inside a 1.5 ml Eppendorf tube. In the prepared tube, the DEAE paper is washed twice with 150 μl low salt buffer (0.1M NaCl, 10 mM Tris pH 8.0, 1 mM EDTA), by mashing the paper in the liquid and then drawing out the liquid through the hole in the bottom by centrifugation. This is followed by 4 washes in 75 μl high salt buffer (1.0M NaCl, 10 mM Tris pH 8.0, 1 mM EDTA). The high salt washes are pooled and extracted once with an equal volume of phenol:chloroform 1:1, and once with chloroform. DNA is precipitated by addition of 2 or more volumes of 95% ethanol, frozen in a dry ice-ethanol bath for 15 min, and centrifuged for 10 min at 4° C. The supernatant is carefully removed, and the pellet dried and resuspended in an appropriate volume of TE.

9. Preparation of competent *E. coli* cells using RbCl: *E. coli* cells are grown in liquid culture to mid-log phase (Klett=60 to 80), chilled on ice, and harvested by centrifugation in a Beckman JA-14 rotor at 4000 rpm for 5 min. Cells are resuspended in 1/5 volume TFB I (30 mM potassium acetate, 100 mM RbCl, 10 mM $CaCl_2$, 50 mM $MnCl_2$, 15% glycerol, pH 5.8 with 0.2M acetic acid), chilled and harvested as before. Cells are resuspended in 1/50 original volume TFB II (10 mM MOPS, 75 mM $CaCl_2$, 10 mM RbCl, 15% glycerol, pH 6.5 with KOH) and chilled 15 to 60 min on ice before use.

The same transformation protocol described for $CaCl_2$ treated cells is followed for RbCl treated cells.

10. Phage assay for methylation: 20 ml of Rich broth (Per liter, Rich broth contains: 10 g tryptone; 5 g yeast extract; 5 g NaCl; pH adjusted to 7.0 with 1N NaOH) with 0.04% maltose and appropriate antibiotics are inoculated 1:100 with an overnight culture of the transformant. The new culture is grown to mid-log phase at 37° C. with shaking, and the cells are harvested by centrifugation (4000 rpm 5 min) and resuspended in 1 ml SM (100 mM NaCl, 8 mM $MgSO_4 \cdot 7H_2O$, 50 mM Tris-HCl pH 7.5, 0.01% gelatin). $\lambda_{vir}$ phage are added to a multiplicity of infection of 10, and the cells incubated at 37° C. for 20 min to allow phage adsorption. Following incubation, the volume is restored to 20 ml by addition of Rich broth containing 0.04% maltose, and the culture is grown at 37° C. overnight. The next day, 200 μl of chloroform is added to the culture, cell debris is removed by centrifugation followed by filtration through a 0.45 μm filter (Schleicher and Schuell). Phage DNA is isolated from 1 ml of clarified supernatant by extraction with phenol then chloroform, precipitation with ethanol at $-70°$ C., followed by centrifugation (12000 rpm 20 min in a Beckman JA-17 rotor), and resuspension of the pellet in 100 μl TE containing 20 μg/ml RNase.

---

What is claimed is:

1. Isolated DNA coding for the BglII restriction endonuclease, wherein the isolated DNA is obtainable from ATCC Accession No. 69247.

2. A recombinant DNA vector comprising a vector into which a DNA segment coding for BglII endonuclease produced by *Bacillus globigii* has been inserted.

3. Isolated DNA coding for the BglII restriction endonuclease and methylase, wherein the isolated DNA is obtainable from ATCC Accession No. 69247.

4. A cloning vector which comprises a vector into which the isolated DNA of claim 1 has been inserted.

5. A cloning vector which comprises a vector into which the isolated DNA of claim 3 has been inserted.

6. A prokaryotic host cell transformed by the vector of claim 2, 4 or 5.

7. A method of producing BglII restriction endonuclease comprising culturing a prokaryotic host cell protected against BglII cleavage transformed with the vector of claim 2, 4 or 5 under conditions suitable for the expression of said endonuclease.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:1:

```
Met  Lys  Ile  Asp  Ile  Thr  Asp  Tyr  Asn  His  Ala  Asp  Glu  Ile  Leu  Asn
 1             5                        10                       15
```

( 2 ) INFORMATION FOR SEQ ID NO:2:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:2:

| ATYTCRTCNG | CRTGRTCRTA | R | | | | 21 |
|---|---|---|---|---|---|---|

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:3:

| ATGAARATHG | AYATHAC | | | | | 17 |
|---|---|---|---|---|---|---|

(2) INFORMATION FOR SEQ ID NO:4:

(i) SEQUENCE CHARACTERISTICS:
        (A) LENGTH: 3188 base pairs
        (B) TYPE: nucleic acid
        (C) STRANDEDNESS: single
        (D) TOPOLOGY: linear (xi) SEQUENCE DESCRIPTION: SEQ ID NO:4:

| CTGCAGGAAG | TTGCTATTTT | GGAGAGTTTG | CGGGAGTATC | GGTATATGAA | GTGAGGGATA | 60 |
|---|---|---|---|---|---|---|
| TGGGGTTCAG | AGATGGCATT | CTCTGGGCTC | TTTTTTGCGC | ATTTTTCATT | TAGTACAGCA | 120 |
| AATTGCTAAT | TAGTTTGGTT | ATTTCCAGCG | AGCAACTCGG | TGAGTCCATC | TCGTTCAATT | 180 |
| AAAGCTCCCA | CTCACACCCA | AGTCCTTGAA | TGTTTCAATC | AGTTGTAGTC | CTTTTACTTT | 240 |
| GCAGTATTCG | TTGATGGCAT | TTTCTTGAAC | GTCTTTTCCA | TAACCTTTTT | CAGCTTGCGT | 300 |
| TTCAGTTGAA | ACACGAACAT | AACCAAAAAC | CTTTTCCATC | CACACACCAT | CTTCCTTAAC | 360 |
| TTGTAAATGA | GTATAGGACC | TCTCGTTATC | TTTGTAAACT | CCTATGTATA | AGATTTTATT | 420 |
| AAAAAGCCTT | AACATCGTTT | TATTTAAAGG | TTTTTATTTG | TTTTTCTTGT | TTTTATCGCT | 480 |
| TCTGTTATCA | TGTCAAGGGA | ATCATTTTAT | CTACGATAGA | TACTTATAGT | CCGTGGACAC | 540 |
| ATAGTCATCA | AAAGAGTACC | TTTGATTGTA | GTATTTAGGT | GGTGAATTTT | ATGGACATTA | 600 |
| GAGAAAGGTT | CGGAAAGACT | GTTTCTTCTA | TAAGAAGAAA | GCAAAACCTT | TCACAAGAAA | 660 |
| AACTAGCAGA | AATATCCAAA | TTAGACCGCA | CTTACATAGG | CGGTGTAGAA | CGTGGAGAAC | 720 |
| GCAATCTATC | ACTTCTTAAC | ATCGAGAGAC | TCTCAAATGC | TCTACAAATG | GAAATATCAG | 780 |
| AGGTATTCAG | ATTGATGGAA | GGAGACACTC | ATAATGAAGA | TTGATATAAC | GGACTATAAC | 840 |
| CATGCTGATG | AAATACTAAA | TCCTCAATTA | TGGAAAGAAA | TTGAAGAAAC | GCTATTAAAA | 900 |
| ATGCCATTAC | ACGTTAAAGC | ATCAGATCAA | GCCAGCAAAG | TTGGCAGTTT | AATTTTTGAT | 960 |
| CCTGTCGGTA | CAAATCAATA | CATAAAAGAT | GAGTTGGTAC | AAAACATTG | GAAAAATAAT | 1020 |
| ATCCCTATAC | CTAAACGATT | TGACTTCCTA | GGTACTGACA | TAGATTTTGG | TAAAAGAGAT | 1080 |
| ACGCTAGTTG | AAGTTCAGTT | TTCTAATTAC | CCATTTCTGC | TCAATAATAC | GGTACGTTCA | 1140 |
| GAACTGTTTC | ATAAAAGTAA | CATGGACATT | GATGAAGAAG | GAATGAAAGT | AGCGATCATT | 1200 |
| ATTACTAAAG | GGCATATGTT | TCCCGCTTCT | AACAGTTCAT | TATATTATGA | ACAAGCTCAA | 1260 |
| AATCAACTTA | ACTCCTTAGC | TGAATATAAC | GTTTTGATG | TACCTATAAG | ATTAGTAGGG | 1320 |
| TTAATAGAAG | ACTTTGAAAC | TGATATTGAT | ATTGTTTCAA | CTACATATGC | GGACAAACGC | 1380 |
| TATTCAAGGA | CAATAACAAA | AAGAGATACC | GTTAAAGGTA | AAGTGATTGA | TACCAACACG | 1440 |

-continued

| | | | | | | |
|---|---|---|---|---|---|---|
| CCGAATACCA | GACGTCGGAA | AAGAGGAACA | ATCGTGACAT | ATTAAATTTT | ATTAGACTAC | 1500 |
| TTAATGGTTA | TCTGATAAAC | TTAATATACA | CGATGACTAT | AAGTATCATT | TCGGAGGTAT | 1560 |
| ATTAAGTGAG | TGAAGATCAA | TATAAACAAA | TAAAGTTACA | TTTAGGTATG | AAGATGACA | 1620 |
| ACGAAGACCT | ACCAAACCAC | ATACCGTCAT | CATTTCCTAA | GCAACACCTA | AACAAATAT | 1680 |
| ATAATGGTGA | CACAATGAAC | ATGTTATTAG | ATATACCAGA | CAATTCAGTT | GATTTAGTTG | 1740 |
| TAACTTCACC | ACCTTACAAC | ATTAATAAAT | TTAAAAATGA | TCGCCGACCT | TTAGAAGAAT | 1800 |
| ATCTAAAGTG | GCAAACAGAA | ATTATTGAAC | AATGCCATAG | AGTGTTAAAA | CCAAGTGGAT | 1860 |
| CAATATTTTG | GCAAGTTGGA | ACTTATGTAA | ATGATAGCGG | GGCTCATATA | CCCTTAGATA | 1920 |
| TACGTTTTTT | CCCTATATTT | GAATCGTTAG | GTATGTTTCC | GAGAAATAGG | ATAGTGTGGG | 1980 |
| TTAGACCTCA | CGGATTGCAT | GCTAACAAGA | AGTTTGCTGG | CCGGCATGAA | ACTATTCTTT | 2040 |
| GGTTACAAA | GACACCAGAA | TACAAATTTT | TTTTAGACCC | TATCCGTGTA | CCTCAAAAAT | 2100 |
| ATGCTAACAA | AAAGCATTAT | AAAGGGGATA | AAAAAGGAGA | ACTTTCTGGA | GACCCATTGG | 2160 |
| GTAAAAATCC | TGGTGATGTT | TGGGCATTTA | GAAACGTAAG | GCATAACCAT | GAAGAAGATA | 2220 |
| CCATACACCC | AACCCAATAT | CCAGAAGACA | TGATAGAAAG | AATCGTTTTG | AGCACAACAG | 2280 |
| AACCTAATGA | TATTGTACTA | GATCCATTTA | TAGGTATGGG | TACGACTGCA | AGTGTTGCTA | 2340 |
| AAAATCTAAA | CAGATATTTC | TATGGGGCTG | AGATTGAAAA | AGAATATGTG | GATATTGCCT | 2400 |
| ATCAAATACT | GTCGGGGGAG | CCAGACGAAA | ATAATAACTT | CCCTAACCTA | AAAACGTTAC | 2460 |
| GTCAATACTG | TGAGAAAAAT | GGCATAATTG | ATCCTAGCCA | ATACACTTTT | ACGAGACAGC | 2520 |
| GAAAGGAAG | TAAACCTTCT | CTAGACAGCA | AAGCACATCC | AGAAGAGCAC | CACAAAAAAG | 2580 |
| AGATTGTAGA | AAGAATAGAA | TTTGAAGCAG | AAAACTCTGT | ATATAAAAAA | GTTCAAAATG | 2640 |
| AACAATAAAA | TGGCGGTAAT | GATACCGTCA | TTTTTTTATC | AAAGTTTTCA | CTCCTTTCTT | 2700 |
| CTGCCCTTGT | ACAACAGCTA | TAAGATTTTT | TGTTATTTGT | GTTTCTCGTA | TTGTCTTTTT | 2760 |
| TAACTTCTTG | TGTTTACTCC | ATATAATAAA | AAGAACAACC | AACGAGAAAT | GGTTGCTCTT | 2820 |
| ACGCCTGCTT | TATTTTGATA | GTTGCATTAA | ACTTATTTCG | TCTTATGTCG | TTGTTCCCTT | 2880 |
| ACTTTGAAAT | AATATCTACT | AGATTATCTC | AACAACTTGT | ATCATCGCTT | GTTTCTTTAG | 2940 |
| CAGATAGTTC | TCTATTTTCT | CTAATCAGTT | CGTAGGTTCT | TACATCAATT | CTTGTTAATG | 3000 |
| CTTCTTCTAG | GCGATCAATA | AACTTGTAAT | TAGGCTTTTC | CTTACTTAAT | TATTCATTAT | 3060 |
| AACGTTGCAT | TAATCGCCTT | GTCCATATTT | TTAGCAGCTT | GTACCGACCT | TTAACTTGCT | 3120 |
| TTTCCTCCAT | ATCCTTAAAG | TGCTCTAATA | ATCGATTTTT | GTATTCTTCT | ATAGAAATCA | 3180 |
| GCGTTGAC | | | | | | 3188 |

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGAGACACTC    TCATGAAGAT    T                            2 1

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGTTTATATG GATCCTCACT CAC 23